US008282849B2

(12) United States Patent
Morisawa et al.

(10) Patent No.: US 8,282,849 B2
(45) Date of Patent: Oct. 9, 2012

(54) ETCHING PROCESS STATE JUDGMENT METHOD AND SYSTEM THEREFOR

(75) Inventors: Toshihiro Morisawa, Yokohama (JP); Shoji Ikuhara, Hikari (JP); Akira Kagoshima, Kudamatsu (JP); Daisuke Shiraishi, Hikari (JP)

(73) Assignee: Hitachi High-Technologies Corporation, Tokyo (JP)

( * ) Notice: Subject to any disclaimer, the term of this patent is extended or adjusted under 35 U.S.C. 154(b) by 363 days.

(21) Appl. No.: 12/385,273

(22) Filed: Apr. 3, 2009

(65) Prior Publication Data

US 2009/0253222 A1 Oct. 8, 2009

(30) Foreign Application Priority Data

Apr. 4, 2008 (JP) ................................. 2008-098111

(51) Int. Cl.
G01L 21/30 (2006.01)
(52) U.S. Cl. ..................................... 216/59; 156/345.24
(58) Field of Classification Search .................. None
See application file for complete search history.

(56) References Cited

U.S. PATENT DOCUMENTS

| 6,077,386 A * | 6/2000 | Smith et al. ............. 156/345.24 |
| 2004/0004708 A1 | 1/2004 | Willis |
| 2006/0287753 A1 | 12/2006 | Plumhoff |

FOREIGN PATENT DOCUMENTS

| JP | 08-062141 | 3/1996 |
| JP | 2005-527983 | 9/2005 |
| JP | 2006-91309 | 4/2006 |
| JP | 2006-140237 | 6/2006 |
| JP | 2007-115765 | 5/2007 |
| KR | 2002-0060817 | 7/2002 |
| WO | WO 2006-138199 | 12/2006 |

OTHER PUBLICATIONS

Office Action issued in Japanese Patent Application No. 2008-098111 on Jan. 31, 2012.

* cited by examiner

*Primary Examiner* — Binh X Tran
*Assistant Examiner* — David Cathey, Jr.
(74) *Attorney, Agent, or Firm* — Antonelli, Terry, Stout & Kraus, LLP.

(57) ABSTRACT

An etching process state judgment method comprising: a spectral data obtaining step, in which an optical emission spectrum distribution is obtained by monitoring optical emission during an etching process of a plurality of wafers; a peak detection step, in which peaks are detected from the optical emission spectrum distribution at a specific time point during the etching process, to obtain peak characteristics; a common peak identifying step, in which peaks common to the wafers are identified among the peaks detected in the peak detection step; and a state detection step, in which the characteristics are compared regarding the common peaks, to detect a state of each wafer in the etching process.
A state (anomaly or normalcy) of an etching process is detected from optical emission spectrum distribution at the time of etching process, by a simple method without assuming substances.

9 Claims, 18 Drawing Sheets

FIG. 14

[Original optical emission spectrum] 1401

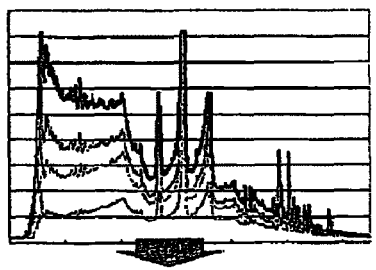

[Spectral ratio] 1411

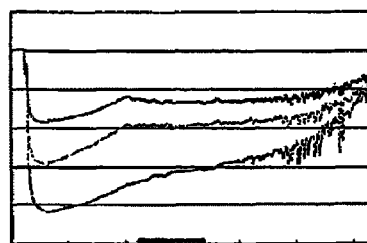

[Moving average of spectral ratio] 1421

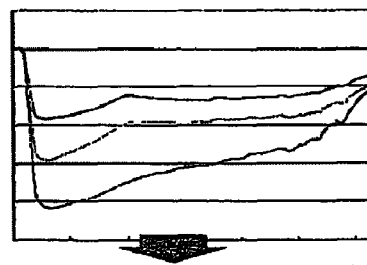

1422
Number of reference points in moving-average operation on one side: 25 [samples]

[Spectral ratio error standard deviation]

1433

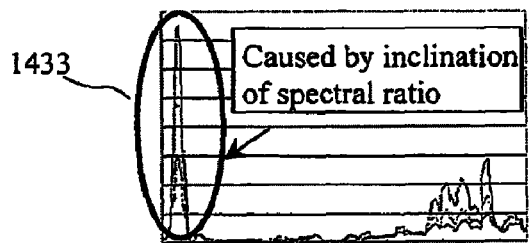

1431
1432
Caused by inclination of spectral ratio
Standard deviation calculation range (one side): 20 [samples]

[Spectral ratio error standard deviation after inclination correction]

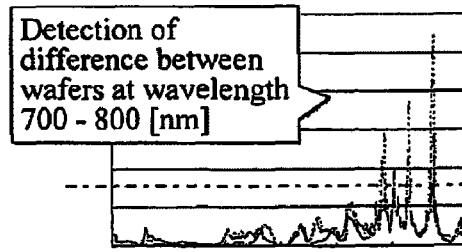

Detection of difference between wafers at wavelength 700 - 800 [nm]

1441

1442
Judgment threshold

ETCHING PROCESS STATE JUDGMENT METHOD AND SYSTEM THEREFOR

The present application claims priority from Japanese application JP 2008-098111 filed on Apr. 4, 2008, the content of which is hereby incorporated by reference into this application.

BACKGROUND OF THE INVENTION

The present invention relates to a technique of judging a state (anomaly or normalcy) of an etching process on the basis of optical emission spectrum distribution obtained by monitoring optical emission of plasma in etching equipment.

To obtain a micro shape of a semiconductor device or the like to be formed on a wafer, an etching process is performed where a substance is ionized by using plasma, and material on the wafer is removed by action (i.e. chemical reaction on the wafer surface) of the ionized substance. Various substances may be used as the substance to be ionized, and the material on the wafer may be different according to the function of the product. Further, to form the shape on the wafer, resist of an organic substance is applied to the wafer, and the shape is formed by photo-lithography, and then the etching process is performed. Further, a substance for adjusting the reaction rate is introduced in order to obtain the predetermined shape. Within a chamber vessel in which the etching process is performed, a variety of substances react with one another.

Ionization by plasma is accompanied by an optical emission phenomenon. Accordingly, etching equipment using plasma in its process is provided with an Optical Emission Spectrometry (OES) to monitor a state of plasma generation.

By monitoring the optical emission phenomenon due to plasma, it is possible to ascertain the performance of the etching process.

Patent Document 1 shows a method in which a plurality of substances are designated, data of the wavelength and magnitude of light emitted by each substance are prepared in a database, and a substance generating a peak is identified. Particularly, Patent Document 1 shows a method in which a learning function improves the accuracy of identification of a substance each time the analysis is performed.

Patent Document 1: Japanese Un-examined Patent Application Laid-Open No. 8-62141

SUMMARY OF THE INVENTION

In Patent Document 1, a peak wavelength is previously defined as a wavelength of a substance. In other words, it is judged whether a peak exists or not at the wavelength of light emitted from a certain substance. Thus, it is impossible to detect a peak if the peak exists at a different wavelength from the wavelengths of light emitted from the prepared substances. Accordingly, it is impossible to judge anomaly or normalcy of an etching process accurately.

Thus, an objective of the present invention is to detect a state (anomaly or normalcy) of an etching process by using a simple method based on optical emission spectrum distribution obtained at the time of the etching process.

To achieve the above objective, an etching process state judgment method of the present invention comprises: a spectral data acquiring step, in which an optical emission spectrum distribution is obtained by monitoring optical emission during an etching process of a plurality of wafers; a peak detection step, in which peaks are detected from the optical emission spectrum distribution at a specific time point during the etching process, to obtain peak characteristics; a common peak identifying step, in which peaks common to the wafers are identified among the peaks detected in the peak detection step; and a state detection step, in which the characteristics are compared regarding the common peaks, to detect a state of each wafer in the etching process.

Further, an etching process state judgment method of the present invention may comprise a spectral data acquiring step, in which an optical emission spectrum distribution is obtained by monitoring optical emission during an etching process of a plurality of wafers; a peak detection step, in which peaks are detected from the optical emission spectrum distribution at a specific time point during the etching process, to obtain peak characteristics; and a state detection step in which: an optical emission spectrum distribution of a previously-determined baseline wafer is taken as baseline, and a spectral ratio of an optical emission spectrum distribution of another wafer with respect to the baseline is obtained at each wavelength position; a standard deviation of the spectral ratio is obtained at each of wavelength positions arranged at intervals of a prescribed width; a derivative of the spectral ratio is obtained at each of the wavelength positions arranged at intervals of the prescribed width; a dispersion index is obtained by dividing the standard deviation by an absolute value of the derivative at each of the wavelength positions arranged at intervals of the prescribed width; and a change of a state of the another wafer with respect to the criterion wafer for baseline is detected on a basis of the dispersion index.

According to the present invention, a state (anomaly or normalcy) of an etching process can be detected from optical emission spectrum distribution at the time of etching process, without assuming a substance.

BRIEF DESCRIPTION OF THE DRAWINGS

FIG. 14 is an explanatory diagram showing an anomaly/normalcy judgment method based on dispersion of spectral ratio errors;

DESCRIPTION OF PREFERRED EMBODIMENTS

Figure 1:
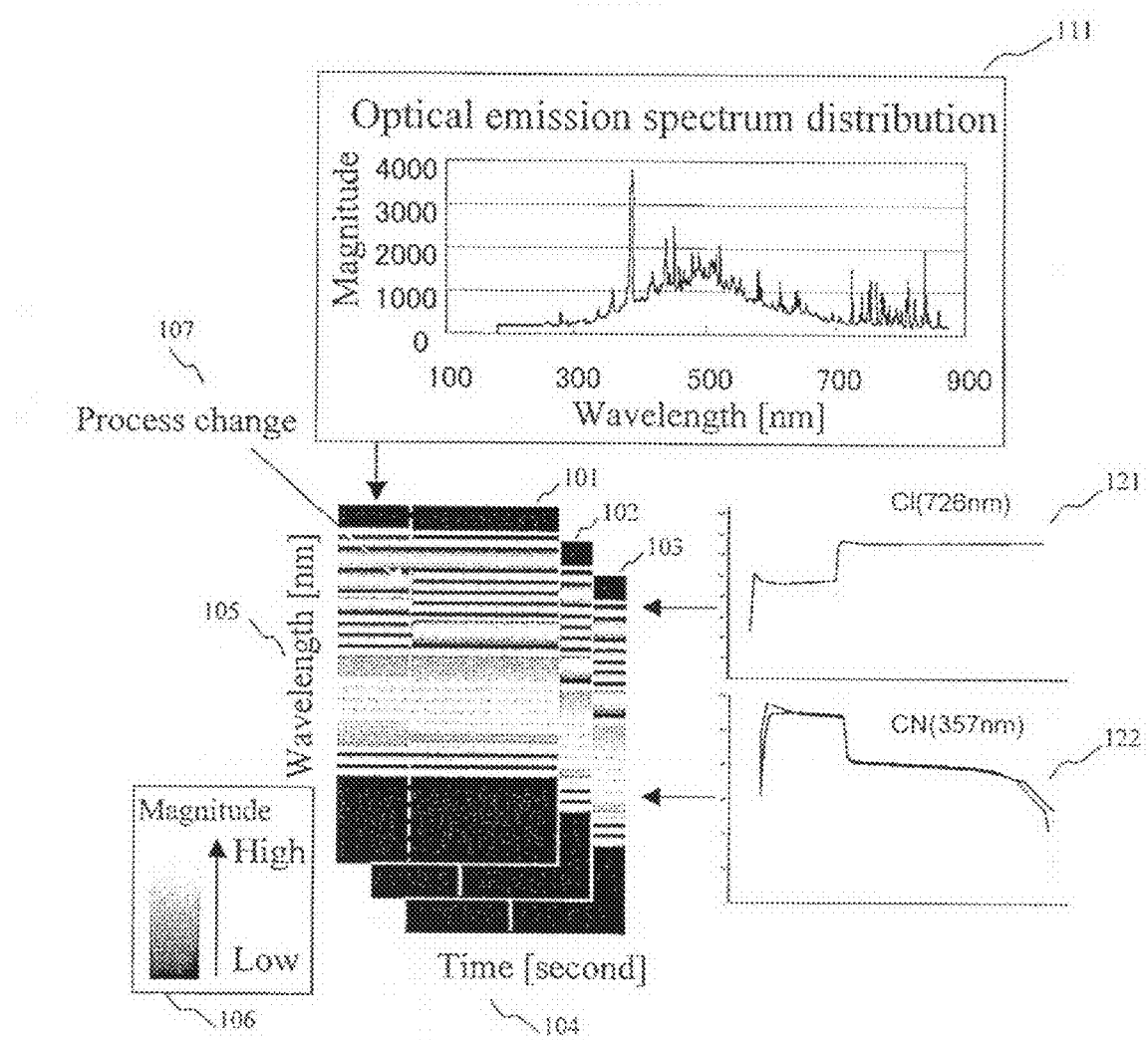
FIG. 1 is a diagram for explaining optical emission spectrum distribution obtained by an optical emission spectrometry (OES)

Now, one embodiment of the present invention will be described referring to the drawings.

First, an optical emission spectrum distribution will be described.

FIG. 1 shows an optical emission spectrum distribution obtained by an optical emission spectrometry (OES). An optical emission spectrum distribution with time 104 on the x-axis and wavelength 105 on the y-axis can be expressed as a bitmap.

Bitmaps 101, 102 and 103 depict optical emission phenomena concerning a plurality of wafers. From an optical emission spectrum distribution 111 at a certain point of time, it is seen that the distribution is convex in the large in the neighborhood of the center of monitored wavelengths, and peaks exist at many wavelength positions.

Further, from emission magnitude (waveform) graphs 121 and 122, it is seen that the emission magnitude varies as the etching process proceeds, and the optical emission phenomenon changes at the time of process change 107.

By monitoring this optical emission phenomenon due to plasma, it is possible to ascertain the performance of an etching process. For example, at the time of equipment's start-up, it is possible to inspect the etching process by judging whether prescribed reaction is occurring. Or, in the case of high-volume manufacturing, it is possible to detect anomaly by monitoring the emission magnitude in consecutive-work of wafers. Further, an optical emission distribution is utilized for end-point detection in which the end time of an etching process is judged. In particular, by utilizing an optical emission distribution, an etching state can be monitored during and in parallel with the etching process. Thus, to perform efficient judgment of an optical emission state and to use in high-volume manufacturing, it is important that an optical emission state can be judged automatically each time of a wafer processing.

Further, since an object of etching is to realize a prescribed shape on a wafer, it is extremely important to determine a relation between an optical emission state and a shape or a rate of etching reaction (i.e. etching rate) so that the result of an etching process can be predicted from data of optical emission.

Figure 2:
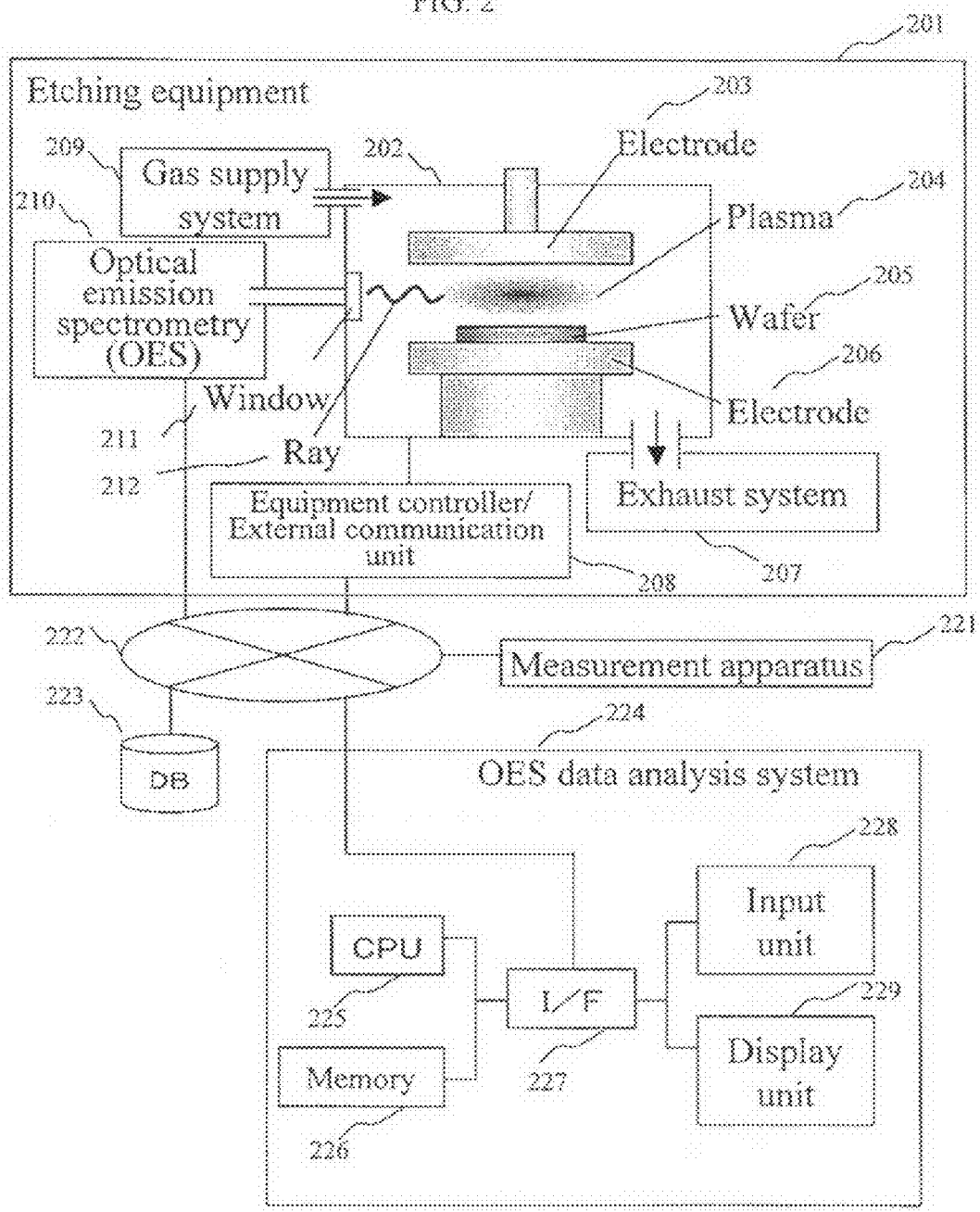
FIG. 2 is a block diagram showing a state judgment system for an etching process.

FIG. 2 is a block diagram showing a configuration of an etching process judgment system according to one embodiment of the present invention.

The etching process judgment system comprises etching equipment 201, a database (DB) 223, an OES data analysis system 224, and a measurement apparatus 221. These component units are coupled with one another through a network 222.

In the etching equipment 201, a chamber 202 is provided, and etching is performed within the chamber 202. A wafer 205 is put and located between electrodes 203 and 206. By generating plasma between these electrodes 203 and 206, the surface of the wafer 205 is etched.

The plasma is accompanied by optical emission. As for this ray 212, emission magnitude at each wavelength of the ray 212 is detected by an optical emission spectrometry (OES) 210. The optical emission spectrometry (OES) 210 receives ray from the inside of the chamber 202 through a window 211.

The optical emission spectrometry (OES) 210 and an equipment controller/external communication unit 208 are coupled with the database DB 223 through the network 222, so that OES data (data showing optical emission spectrum distribution) and data on the etching process are stored in the DB 223.

Further, the measurement apparatus 221 measures a line width and a film thickness of a wafer pattern of before/after the etching process. The measurement apparatus 221 is coupled with the network 222 and the measurement result is stores in the DB 223.

The OES data analysis system 224 judges anomaly or normalcy of the etching process by analyzing the OES data stored in the DB 223, data regarding the etching process and the measurement result.

The OES data analysis system 224 is implemented by a general-purpose-computer comprising a Central Processing Unit (CPU) 225 as an operation unit, a memory 226 such as a Random Access Memory (RAM), an auxiliary storage (not shown) such as a Hard Disk Drive (HDD), an input unit 228 for receiving an input value or an instruction from an operator, a display unit 229 such as a liquid crystal display, and a communication interface 227 with the outside. Each component and function shown in FIG. 3 described below is realized when the CPU 225 executes a prescribed program loaded into the main memory 226. Such a program may be previously stored in the auxiliary storage, or may be read from an external apparatus through the network and executed.

Figure 3:
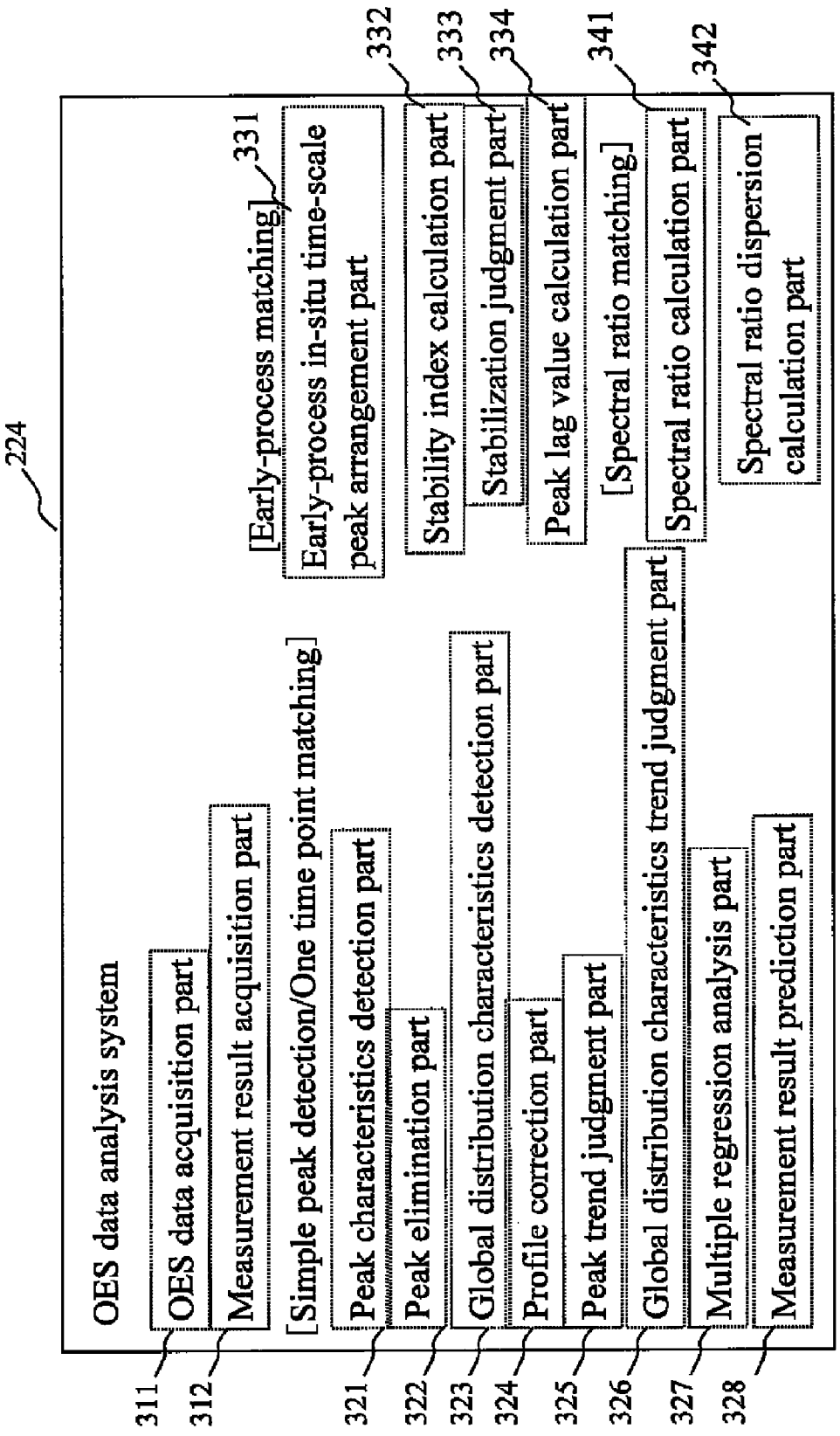
FIG. 3 is a functional block diagram showing an OES data analysis system.

FIG. 3 is a functional block diagram showing the OES data analysis system 224 of the present system.

The OES data analysis system 224 comprises, as its functional parts, an OES data acquisition part 311, a measurement result acquisition part 312, a peak characteristics detection part 321, a peak elimination part 322, a global distribution characteristics detection part 323, a profile correction part 324, a peak trend judgment part 325, a global distribution characteristics trend judgment part 326, a multiple regression analysis part 327, a measurement result prediction part 328, an early-process in-situ time scale peak arrangement part 331, a stability index calculation part 332, a stabilization judgment part 333, a peak lag value calculation part 334, a spectral ratio calculation part 341, and a spectral ratio dispersion calculation part 342.

The OES data acquisition part 311 acquires OES data of a wafer as the analysis object from the database 223.

The measurement result acquisition part 312 acquires from the database 223 measurement result (a pattern shape, an etch rate, and the like) about the wafer as the analysis object.

The peak characteristics detection part 321 automatically detects peaks from an optical emission spectrum distribution and obtains peak characteristics.

The peak trend judgment part 325 extracts peaks that are common among wafers (i.e. peaks due to the same causative substances of optical emission) from the peaks detected by the peak characteristics detection part 321. Then, based on the characteristics of the common peaks, the peak trend judgment part 325 judges a state (anomaly or normalcy) of each wafer in the etching process.

The peak elimination part 322 eliminates the peaks detected by the peak characteristics detection part 321, to obtain an optical emission spectrum distribution after the peak elimination.

The global distribution characteristics detection part 323 extracts a plurality of magnitudes at prescribed wavelength positions from the optical emission spectrum distribution after the peak elimination, to obtain global distribution characteristics showing a global variation in the optical emission spectrum distribution.

The global distribution characteristics trend judgment part 326 compares global distribution characteristics, to judge a state (anomaly or normalcy) of each wafer in the etching process.

The profile correction part 324 corrects original optical emission spectrum distribution by using the global distribution characteristics. In detail, first the profile correction part 324 uses the global distribution characteristics of optical emission spectrum distribution of a previously-determined wafer of baseline to obtain a ratio to the baseline of the global distribution characteristics of optical emission spectrum distribution of another wafer as the object of correction all over the wavelength area (i.e. at each prescribed wavelength position). Then, the original optical emission spectrum distribution of the wafer as the correction object is multiplied by the obtained ratios all over the wavelength area (i.e. at the respective prescribed wavelength positions). By this operation, a corrected optical emission spectrum distribution, from which difference between wafers has been eliminated, is obtained.

The spectral ratio calculation part 341 obtains spectral ratios between optical emission spectrum distributions of a plurality of wafers. In detail, the spectral ratio calculation part 341 determines an optical emission spectrum distribution that becomes baseline (for example, an optical emission spectrum distribution whose average emission magnitude is maximum), and obtains a spectral ratio of another wafer's optical emission spectrum distribution to the baseline optical emission spectrum distribution all over the wavelength area (i.e. at each prescribed wavelength position).

The spectral ratio dispersion calculation part 342 judges anomaly or normalcy of the etching process of the wafer on the basis of the spectral ratio obtained at each specific wavelength by the spectral ratio calculation part 341. In detail, the spectral ratio dispersion calculation part 342 obtains a standard deviation of spectral ratio for every prescribed wavelength range, obtains a differential of spectral ratio, and obtains a dispersion index by dividing the standard deviation by the absolute value of the differential. Then, the spectral ratio dispersion calculation part 342 judges a change of a state of a wafer with respect to the baseline wafer by comparing the dispersion index with a prescribed value, to judge anomaly or normalcy of the etching process.

The multiple regression analysis part 327 obtains a model formula expressing relationship between peaks (peak characteristics obtained by the peak characteristics detection part 321) and measurement results (a pattern shape (a line width, a film thickness and the like), an etch rate and the like measured by the measurement apparatus 221). To specify peaks that have a great influence on the measurement results, the multiple regression analysis part 327 gradually reduces the number of items of peaks in a model formula, and evaluates prediction accuracy among model formulae.

Using the model formula obtained by the multiple regression analysis part 327, the measurement result prediction part 328 predicts measurement results on the basis of OES data of a wafer that becomes the object of prediction of measurement results, to judge anomaly or normalcy of the etching process.

The early-process in-situ time scale peak arrangement part 331 arranges on the time scale each item of peak characteristics (for example, emission magnitude) in the early process of etching of a wafer.

The stability index calculation part 332 calculates a stability index. In detail, the stability index calculation part 332 divides a difference between a peak characteristic (for example, emission magnitude) at each time point and that at the end of the early process by the standard deviation of the peak characteristic on the time scale, squares the quotient, and then obtains the average for the peak characteristics (the sum for all the peak characteristics of one wafer divided by the number of the peak characteristics) at each time point. The obtained average is defined as a stability index.

Based on the stability index, the stabilization judgment part 333 judges a stabilized time point. For example, when the average of stability indexes becomes smaller than a prescribed value or a chi-square critical value at which the degree of freedom becomes a peak number, it is judged that the early process of the etching has become stable.

The peak lag value calculation part 334 obtains a reaction initiation lag value at a peak in the early process of etching. For example, first, each peak is normalized in peak characteristic by setting the maximum value on the time scale to 1 and the minimum value to 0. Then, the peak lag value calculation part 334 obtains the square of a difference between a normalized peak characteristic of a certain wafer as baseline and a normalized peak characteristic of another wafer at the same wavelength position, while shifting time of the normalized peak characteristic of the later wafer. Further, the square of difference between peak characteristics is time-averaged over the range where the baseline normalized peak characteristic overlaps in time with the time-shifted normalized peak characteristic of a wafer other than the baseline wafer, and the amount of shifted time in the case where the time-average of the square of difference becomes minimum is defined as a lag or lead, to obtain a lag value. Anomaly or normalcy of etching process is judged based on the magnitude of the lag value.

Next, a flow of processing in which anomaly or normalcy of an etching process is judged will be described.

The present embodiment has first through third modes as a method of judging anomaly or normalcy of an etching process. An instruction from an operator determines which mode is employed.

[First Mode]

In the first mode, peaks are automatically detected from an optical emission spectrum distribution in OES data, and anomaly or normalcy of an etching process is judged on the basis of difference in characteristics of peaks common to wafers.

First, a method of detecting peak characteristics will be described.

Although each process described in the following is performed by some functional part shown in FIG. 3 depending on the content of the process, the CPU 225 will be described as the subject, for the sake of simplicity.

Figure 4:
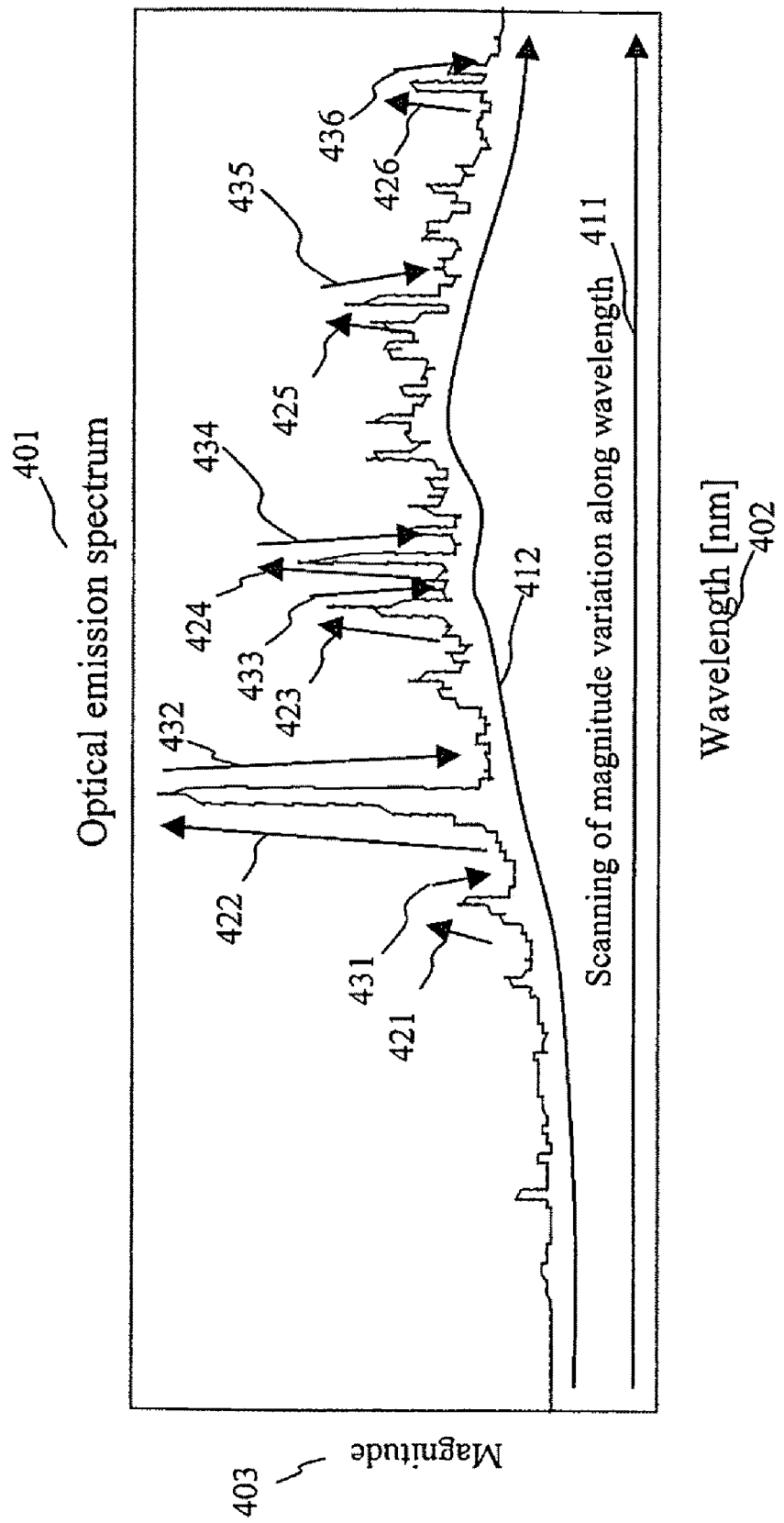
FIG. 4 is a diagram for explaining a peak detection method.

FIG. 4 is a diagram for explaining a method of detecting peaks on the basis of an optical emission spectrum distribution 401.

The CPU 225 scans emission magnitude along wavelength 411, to detect a location where emission magnitude becomes rapidly large. Thus, along the magnitude variation 412, the CPU 225 detects peaks by detecting wavelengths at locations 421, 422, 423, 424, 425 and 462 where magnitude rapidly rises up, and by detecting wavelengths at locations 431, 432, 433, 434, 435 and 426 where magnitude rapidly falls down following respective risings.

Figure 5:
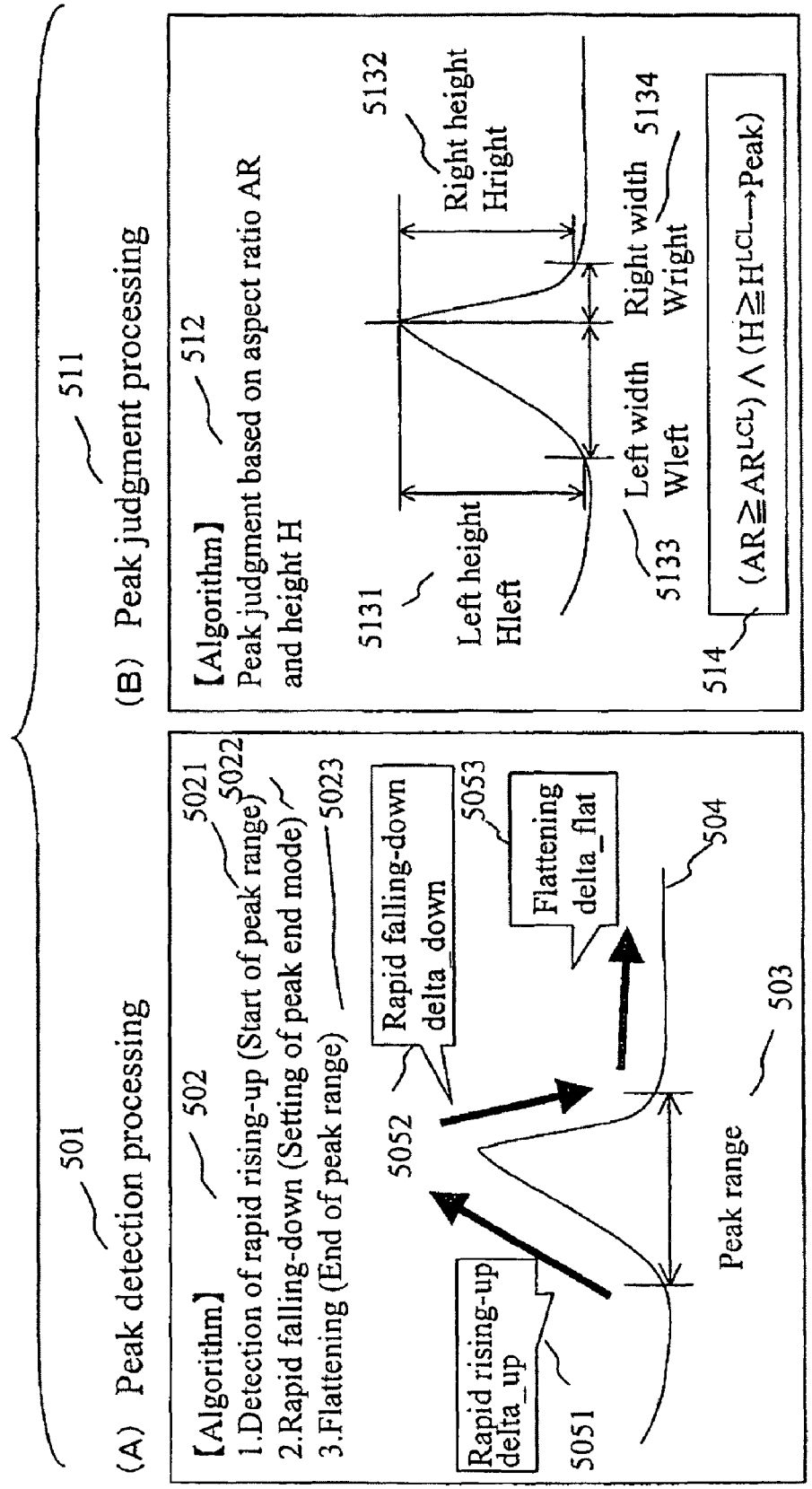
FIG. 5 is a diagram for explaining a peak detection method.

FIG. 5 shows a peak detection method. In this method, the CPU 225 first performs peak detection processing 501 by detecting a variation consisting of rising up and falling down, and then performs peak judgment processing 511 in which peak judgment based on shape is performed.

In the peak detection processing 501, the CPU 225 scans the magnitude 504 along wavelength to detect rapid rising-up 5051, and successively detects rapid falling-down 5052 and thereafter flattening 5053. Such a part is detected as a peak candidate. An interval between the start of the rising-up 5051 and the start of the flattening 5053 becomes a peak range 503.

Then, the CPU 225 performs the peak judgment processing 511 of the peak candidate obtained by the peak detection processing 501.

In detail, the CPU 225 obtains a left height 5131 i.e. a difference between the maximum magnitude and the magnitude at the left end, a right height 5132 i.e. a difference between the maximum magnitude and the magnitude at the right end, a left width 5133 i.e. a difference between the wavelength giving the maximum magnitude and the wavelength of the left end, and a right width 5134 i.e. a difference between the wavelength giving the maximum magnitude and the wavelength of the right end. Then, for each of right and left, the height is divided by the width to obtain an aspect ratio AR. Here, the left end is the start position of the rapid rising-up 5051, and the right end is the start position of the flattening 5053.

When both the obtained aspect ratio and height satisfy prescribed lower limit conditions respectively (514), the CPU 225 judges that the peak candidate in question is a peak. In judgment, an average of the right and left aspect ratios and an average of the right and left heights may be used, for example.

A detected peak has not only the maximum magnitude but also the widths and the heights, and thus peak characteristics are defined.

Figure 6:
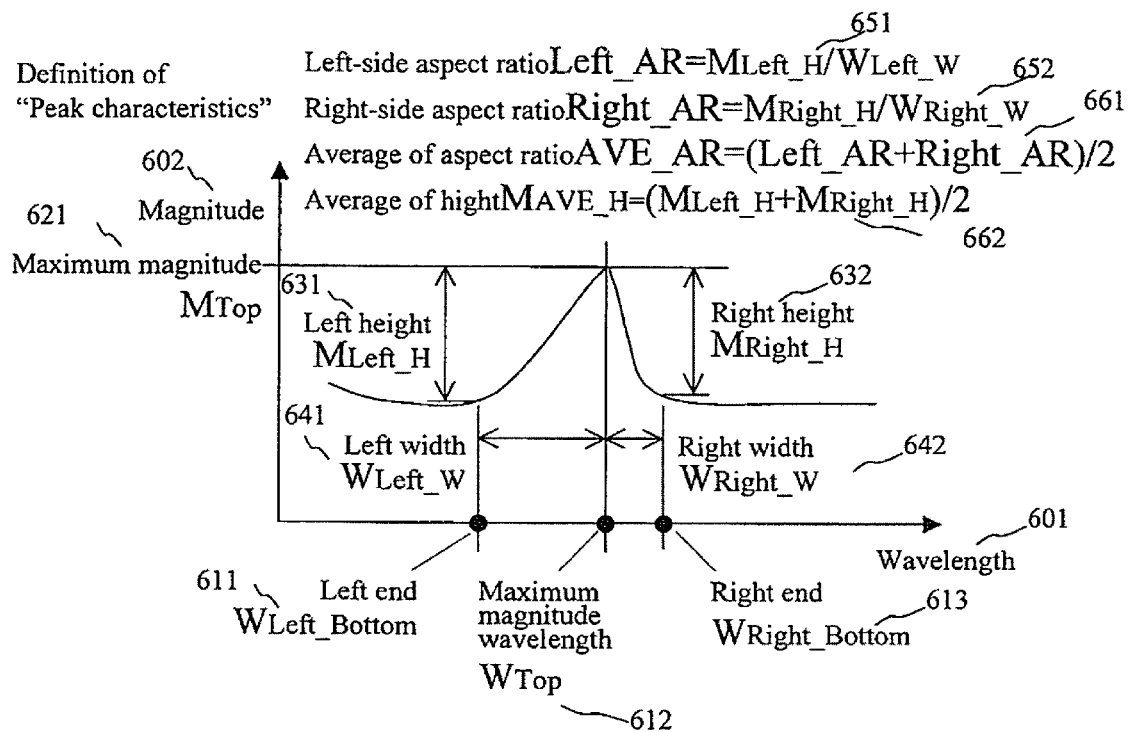
FIG. 6 is a diagram for explaining definitions of peak characteristics.

FIG. 6 is a diagram for explaining definition of peak characteristics.

As values defined as peak characteristics, the following may be mentioned, for example.

Wavelength $W_{Left\_Bottom}$ (referred to as "left-side rising-edge wavelength") at the rising edge on the shorter wavelength side of the peak;

Emission magnitude $M_{Left\_Bottom}$, corresponding to the left-side rising-edge wavelength $W_{Left\_Bottom}$;

Wavelength $W_{Top}$ at which optical emission spectrum distribution magnitude becomes maximum;

Optical emission spectrum distribution magnitude $M_{Top}$ corresponding to the maximum magnitude wavelength $W_{Top}$;

Wavelength $W_{Right\_Bottom}$ (referred to as "right-side rising-edge wavelength") at the rising edge on the longer wavelength side of the peak;

Optical emission spectrum distribution magnitude $M_{Right\_Bottom}$ corresponding to the right-side rising-edge wavelength $W_{Right\_Bottom}$;

Difference $M_{Left\_H}$ (referred to as "left-side peak height") between the maximum value $M_{Top}$ of optical emission spectrum distribution magnitude and the optical emission spectrum distribution magnitude $M_{Left\_Bottom}$ of the left-side rising-edge wavelength;

Difference $M_{Right\_H}$ (referred to as "right-side peak height") between the maximum value $M_{Top}$ of optical emission spectrum distribution magnitude and the optical emission spectrum distribution magnitude $M_{Right\_Bottom}$ of the right-side rising-edge wavelength;

Average $M_{AVE\_H}$ of the left-side peak height $M_{Left\_H}$ and the right-side peak height $M_{Right\_H}$;

Aspect ratio Left_AR (referred to "left-side aspect ratio") obtained by dividing the left-side peak height $M_{Left\_H}$ by the difference $W_{Left\_W}$ between the maximum magnitude wavelength $W_{Top}$ and the left-side rising-edge wavelength $W_{Left\_Bottom}$;

Aspect ratio Right_AR (referred to "right-side aspect ratio") obtained by dividing the right-side peak height $M_{Right\_H}$ by the difference $W_{Rigth\_W}$ between the maximum magnitude wavelength $W_{Top}$ and the right-side rising-edge wavelength $W_{Right\_Bottom}$; and Average AVE_AR of the left-side aspect ratio Left_AR and the right-side aspect ratio Right_AR.

Referring to FIG. 6, regarding the wavelength 601, the left-side rising edge 611, the maximum magnitude wavelength 612, and the right-side rising edge 613 are characteristics. Regarding the magnitude, the maximum magnitude 621 is a characteristic. Regarding the shape, the left height 631, the right height 632, the left width 641, the right width 642, the left aspect ratio 651 and the right aspect ratio 652 are characteristics. Regarding the sharpness and size of the peak, the aspect ratio average 661 and the height average 662 are characteristics.

Next, referring to FIGS. 7 and 8, a method of detecting global distribution characteristics will be described.

Figure 7:
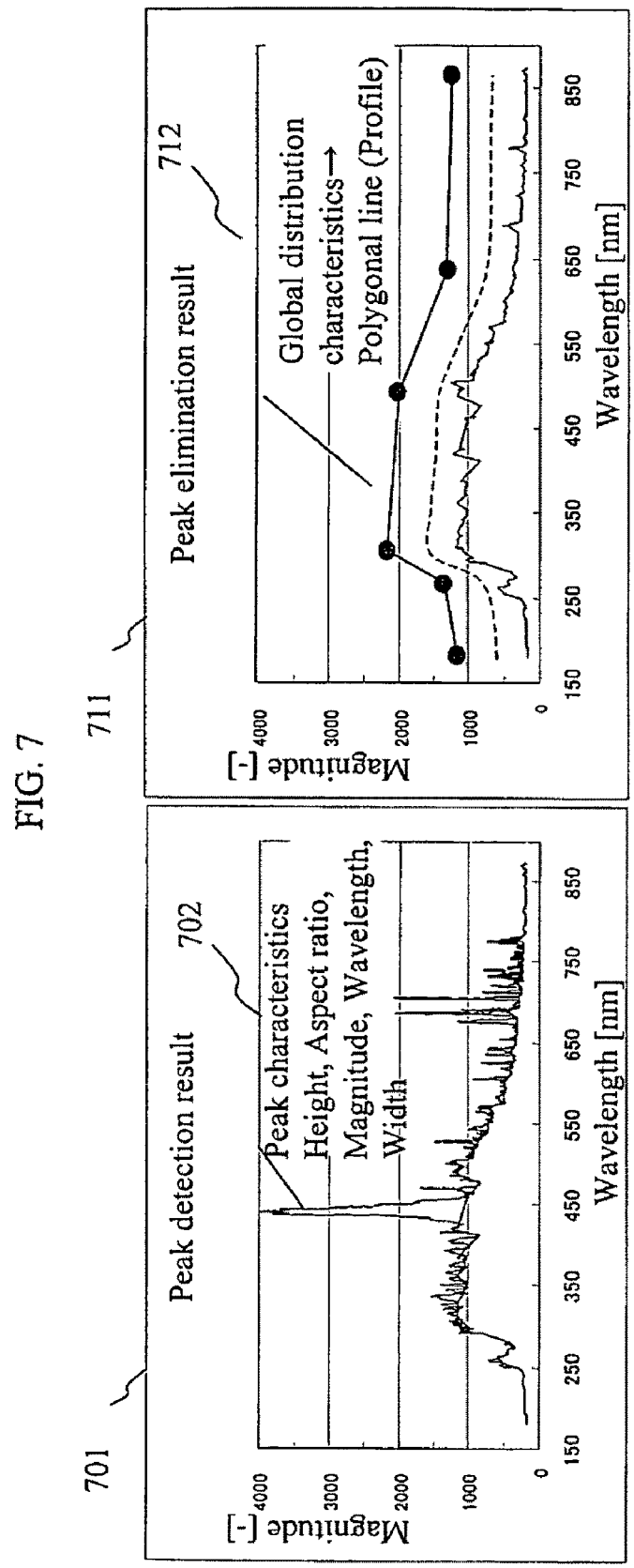
FIG. 7 is a diagram for explaining a method of detecting global distribution characteristics.

In the case where peaks are detected as shown in the graph 701 of FIG. 7, a peak elimination result 711 is obtained by eliminating the detected peaks from the original optical emission spectrum distribution. By defining characteristics of the optical emission spectrum distribution as a whole on the basis of the variation of this optical emission spectrum distribution after elimination of the peaks (i.e. peak-eliminated distribution), global distribution characteristics 712 are obtained.

Since the peak-eliminated distribution becomes gentle in its variation, the distribution can be defined as a polygonal line. Thus, when a pair of wavelength and magnitude is treated as a node, the global distribution characteristics can be expressed a polygonal line connecting nodes.

By suitably determining wavelength positions of X-coordinates of nodes, for example, as 200, 300, 400 (nm) and so on, the CPU 225 can determine the respective magnitudes after elimination of the peaks, to obtain the global distribution characteristics.

Alternatively, global distribution characteristics may be detected by extracting points at which variation of magnitude changes in the peak-eliminated distribution.

Figure 8:
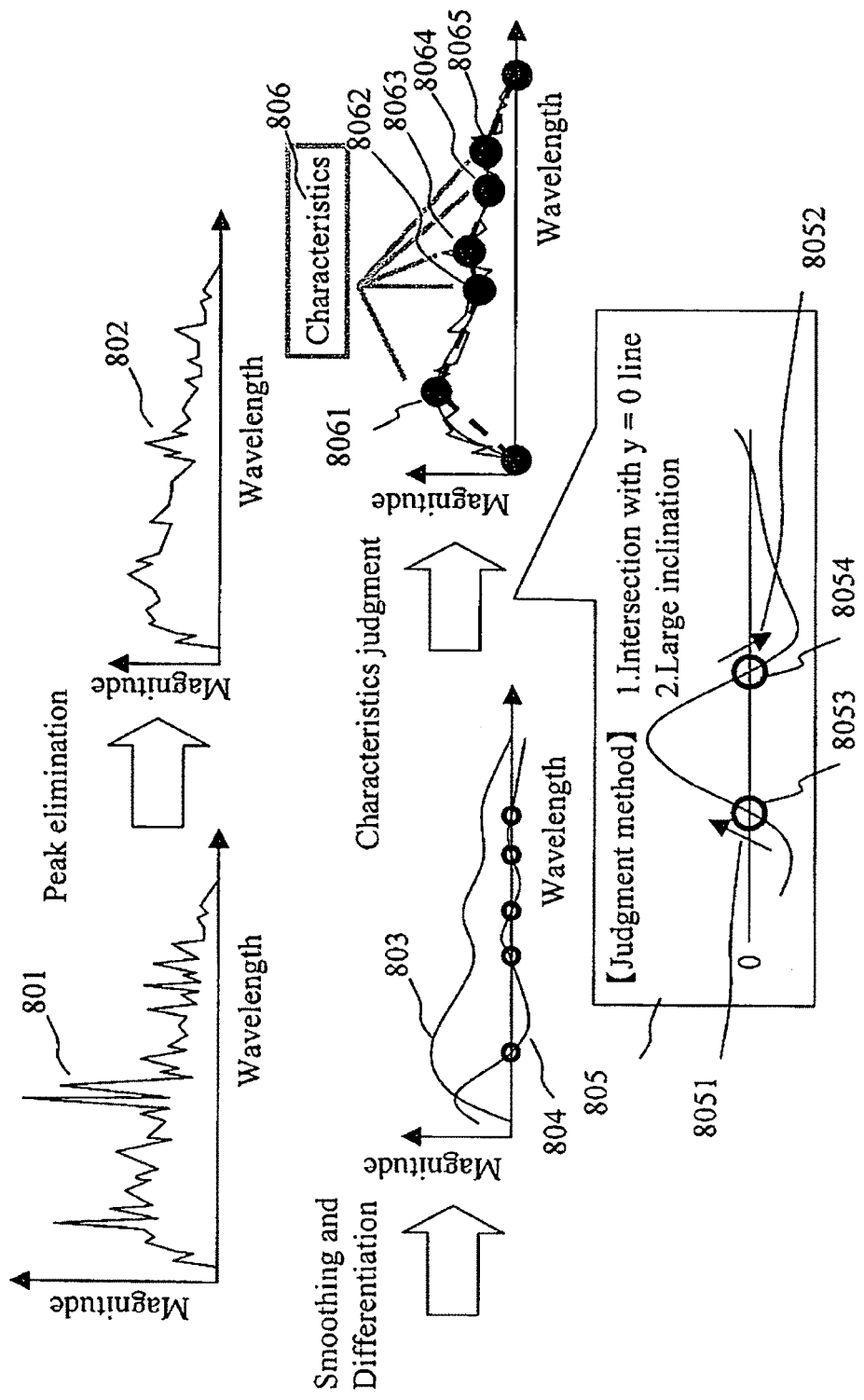
FIG. 8 is a diagram for explaining a method of detecting global distribution characteristics.

FIG. 8 shows an example of a method of detecting global distribution characteristics in such a case.

The CPU 225 obtains a peak-eliminated distribution 802 from the original optical emission spectrum distribution 801. Then, the CPU 225 smoothes the peak-eliminated distribution 802 to obtain a smoothed distribution 803. Further, by differentiating the smoothed distribution 803 in the wavelength direction, a derivative distribution 804 is obtained. Further, at the wavelengths 8051 and 8052 where the magnitude becomes "0" in the derivative distribution 804, magnitudes of inclinations 8053, 8054 are judged. When the magnitude of inclination is larger than a prescribed threshold value (previously-determined threshold value), it is judged that a characteristic (a node) exists in that wavelength position.

In the example shown in FIG. 8, nodes 8061, 8062, 8063, 8064 and 8065 of the polygonal line become global distribution characteristics 806.

The method of obtaining global distribution characteristics can be changed according to an instruction from the operator.

Hereinabove, methods of detecting peak characteristics and global distribution characteristics have been described.

Figure 9:
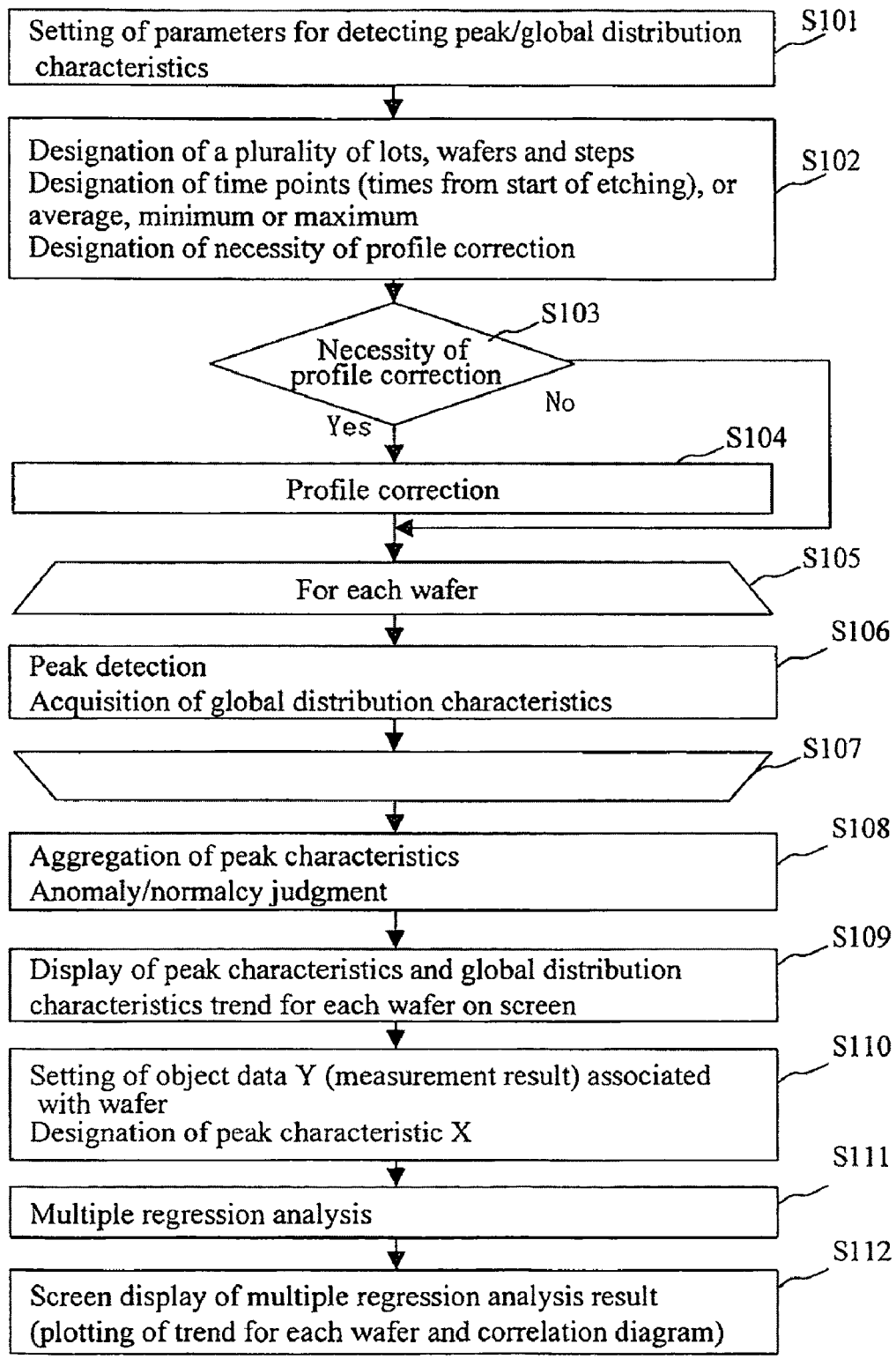
FIG. 9 is a flowchart showing an anomaly/normalcy judgment method.

FIG. 9 is a flowchart showing processing of the first mode of judging anomaly or normalcy of an etching process.

The first mode includes: processing (referred to as "profile correction") of correcting time-series variation relating to the optical emission monitoring system itself, not time-series variation of phenomenon itself of etching at each work; and processing of obtaining a relation between peaks of an optical emission spectrum distribution by multiple regression analysis, to predict a measurement result on the basis of OES data of a prediction object.

First, the CPU 225 sets parameters for detecting peaks and global distribution characteristics, on the basis of input values inputted by the operator through the input unit 228 (Step S101).

In detail, as parameters for peak detection, the CPU 225 sets the threshold value for judging a rapid rising-up 5051, the threshold value for judging a rapid falling-down 5052, the threshold value for judging flattening 5053, the lower limit for the aspect ratio AR, the lower limit for the height H, and the like as shown in FIG. 5(A).

Further, as parameters for detection of global distribution characteristics, the CPU 225 sets a plurality of wavelength positions that become nodes of a polygonal line. Or, in the case where also wavelength positions are automatically detected, the CPU 225 sets the number of reference points in a moving-average operation for smoothing, and threshold values for judging inclinations of a derivative distribution.

Further, the CPU 225 sets a range in which peaks and global distribution characteristics are to be detected. In the processes of detecting peaks and global distribution characteristics, the CPU 225 detects peaks and global distribution characteristics in the set range.

Further, to judge anomaly or normalcy on the basis of peaks and global distribution characteristics, the CPU 225 may previously set control limits for peaks and global distribution characteristics (i.e. an upper limit, a lower limit and a target value for magnitude, and a wavelength range for peaks and nodes of global distribution characteristics). In the case where such control limits are set, the CPU 225 compares characteristics of detected peaks and global distribution characteristics with the respective control limits, to judge anomaly or normalcy of an etching process.

Next, the CPU 225 sets a plurality of wafers that become objects of detection of peaks and global distribution characteristics (Step S102).

Usually, wafers are worked in lots (i.e. units in which a group of wafers are grouped). Thus, the CPU 225 sets an identifier of each lot.

Further, in the case where a film stack is etched in one work in an etching process, processing is performed through a plurality of steps. Thus, the CPU 225 sets steps of the etching process. Further, the CPU 225 sets time points from the start of etching.

Instead of time points, setting may target an average, minimum or maximum optical emission spectrum distribution over the processing time of etching. In such a case, as processing objects in the step S103 and thereafter, the CPU 225 targets the average, minimum and maximum optical emission spectrum distribution obtained over the processing time of etching.

Further, the CPU 225 sets necessity of correction of time-series variation (profile correction) that does not caused by an etching's phenomenon itself.

Then, the CPU 225 reads an optical emission spectrum distribution of OES data satisfying the conditions set in S102, from the database 223, and starts the processing of detecting peaks and global distribution characteristics (Step S103 and the following steps).

First, the CPU 225 judges necessity of the profile correction (Step S103), and performs the profile correction if necessary (Step S104).

Figure 10:
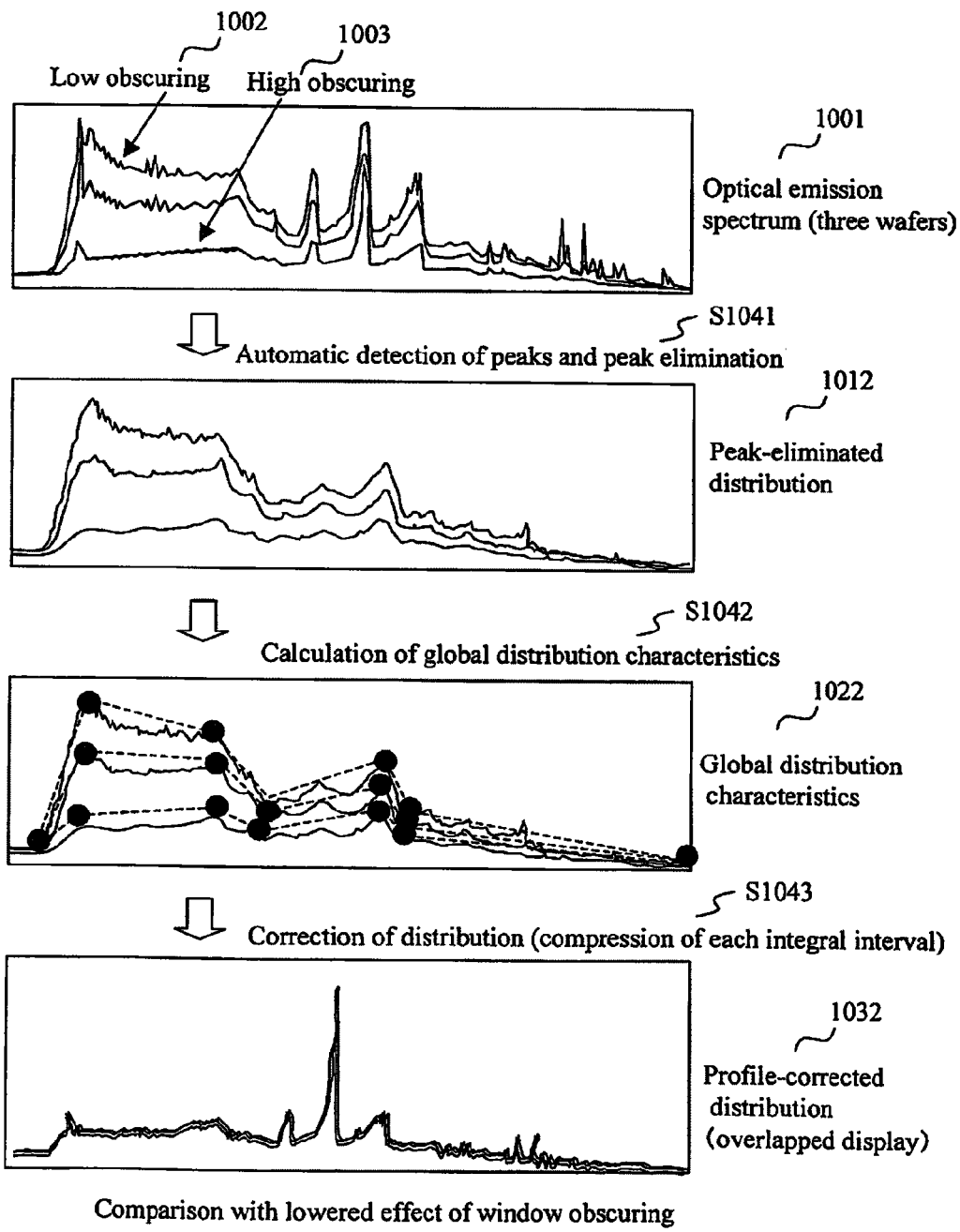
FIG. 10 is a diagram for explaining a profile correction method.

FIG. 10 shows a method of profile correction.

The optical emission spectrum distribution 1001 shown in FIG. 10 shows a case where the window (See the window 211 of FIG. 2) for plasma observation by the optical emission spectrometry becomes obscure owing to adhesion of substance and the observed emission magnitude becomes lowered. The distribution 1002 of higher emission magnitude shows a case where the window obscuring is lower. And, the distribution 1003 of lower emission magnitude shows a case where the window obscuring is higher.

First, the CPU 225 detects peaks by the above-described method, and then obtains a peak-eliminated distribution 1012 (Step S1041).

Further, the CPU 225 obtains global distribution characteristics by the above-described method (Step S1042). Then, for each line segment range of the global distribution characteristics, the CPU 225 compresses the distribution by using a ratio (Step S1043), to obtain a profile-corrected distribution 1032.

In detail, the CPU 225 obtains the magnitude (the following equation (1)) of the baseline global distribution characteristics in a line segment range and the magnitude (the following equation (2)) of the global distribution characteristics as the object of deformation, and uses the ratio between these magnitudes to deform the original optical emission spectrum $$mag_{elim}^{BASE}[i\#] = \frac{mag_{elim}^{BASE}[\text{right}[seg\#]] - mag_{elim}^{BASE}[\text{left}[seg\#]]}{wlen^{BASE}[\text{right}[seg\#]] - wlen^{BASE}[\text{left}[seg\#]]} \times \quad (1)$$
$$(wlen[i\#] - wlen^{BASE}[\text{left}[seg\#]]) + mag_{elim}^{BASE}[\text{left}[seg\#]]$$

$$mag_{elim}^{sample}[i\#] = \frac{mag_{elim}^{sample}[\text{right}[seg\#]] -}{wlen^{BASE}[\text{right}[seg\#]] -} \times \quad (2)$$
$$wlen^{BASE}[\text{left}[seg\#]]$$
$$(wlen[i\#] - wlen^{BASE}[\text{left}[seg\#]]) + mag_{elim}^{sample}[\text{left}[seg\#]]$$

$$mag_{deform}^{sample}[i\#] = \frac{mag_{elim}^{BASE}[i\#]}{mag_{elim}^{sample}[i\#]} \times mag^{sample}[i\#] \quad (3)$$

distribution (the following equation (3)) to compress the distribution.

Here, "mag" indicates emission magnitude, "wlen" wavelength, "i#" index corresponding to wavelength, and "seg#" index corresponding to line segment range. Further, "right" and "left" indicate operations for obtaining indexes corresponding to wavelengths of the right and left ends of the line segment range. A superscript "BASE" added to upper right of a variable means the baseline optical emission spectrum distribution, and "sample" the optical emission spectrum distribution as the object of deformation. A subscript "elim" in lower right means the peak-eliminated distribution, and "deform" the corrected distribution.

As a result of the profile correction, it becomes possible to evaluate subtle difference in optical emission due to etching process itself among wafers. When the profile correction is performed, the CPU 225 performs the following processes (S105-S112) on the corrected optical emission spectrum distribution.

Next, the CPU 225 detects peaks for each wafer by the above-described method, to obtain peak characteristics, and obtains global distribution characteristics (Steps S105-S107).

Then, the CPU 225 aggregates the obtained peak characteristics and global distribution characteristics over the wafers, and judges anomaly or normalcy (Step S108).

Here, the CPU 225 obtains statistics such as the average, maximum, minimum, standard deviation and the like of emission magnitudes of the peaks and global distribution characteristics. However, there is a case where wavelength positions of the peaks and the nodes of the global distribution are slightly different between wafers, or a case where a peak can not be detected. Thus, the CPU 225 performs processing of specifying common peaks to the wafers (i.e. peaks due to same causative substances of optical emission).

Figure 11:
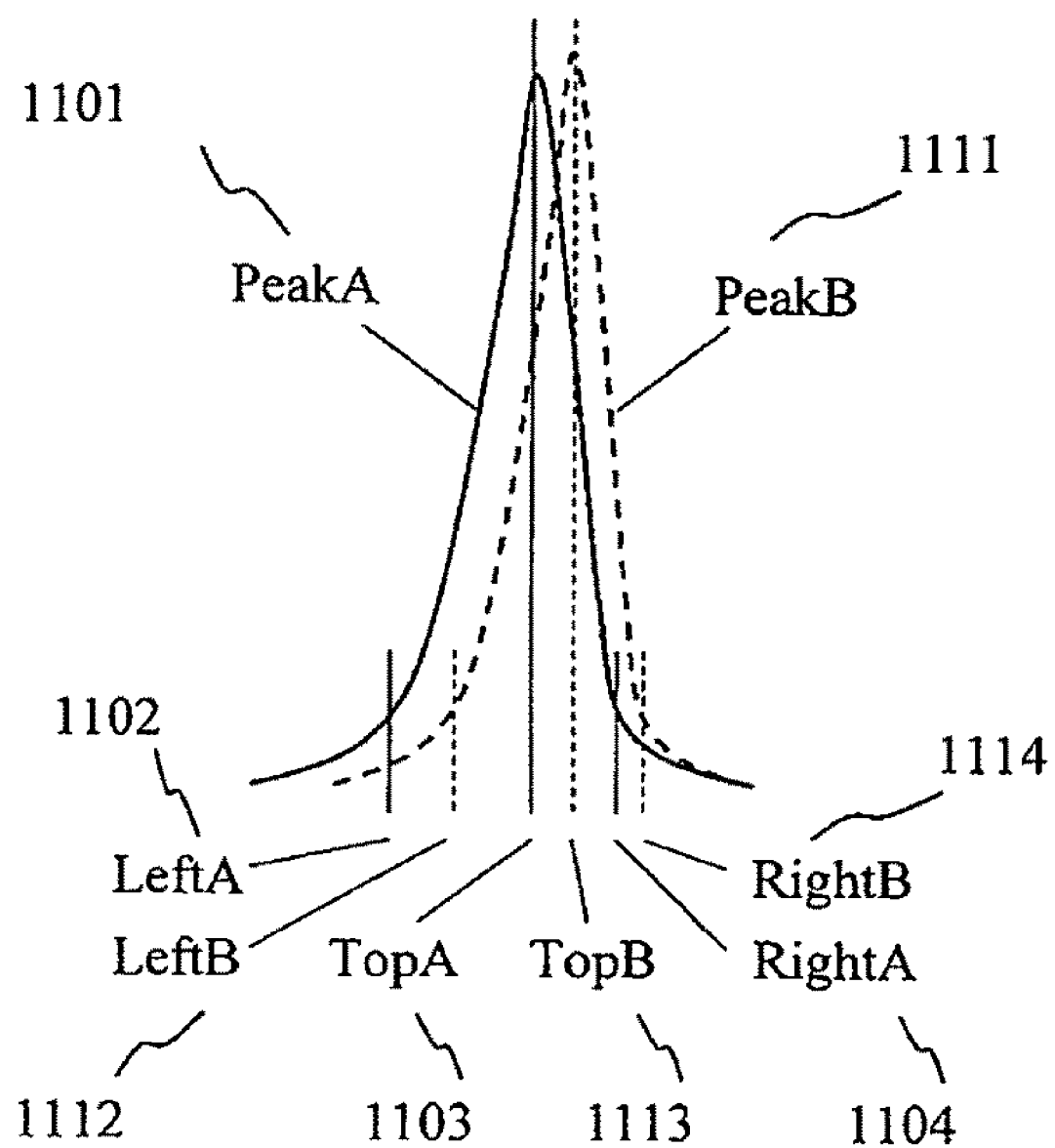
FIG. 11 is a diagram for explaining a method of judging a common peak.

FIG. 11 is a diagram for explaining a method of judging sameness of such peaks. FIG. 11 shows an example where it is judged whether a peak A 1101 of a wafer coincides with a peak B 1111 of another wafer.

The CPU 225 makes a judgment on the basis of the following equations (4) and (5). They express that the CPU 225 judges that both peaks coincide, if the maximum magnitude wavelength TopB 1113 of the peak B exists in the range between the wavelengths LeftA 1102 and RightA 1104 at the left and right end of the peak A.

After the above judgment, the CPU 225 adjusts the baseline range $$\text{LeftA} \leq \text{TopB} \leq \text{RightA:PeakA is as the same as PeakB.} \quad (4)$$

$$\text{TopB} < \text{LeftA} \lor \text{RightA} < \text{TopB: PeakA is different from PeakB.} \quad (5)$$

of the peak A 1101 on the basis of the following equations (6)-(9). This is performed to limit further the peak range in order to judge peak coincidence with still-another wafer.

$$\text{LeftB} > \text{LeftA:new Left is LeftB} \quad (6)$$

$$\text{otherwise: new Left is LeftA} \quad (7)$$

$$\text{RightA} > \text{RightB: new Right is RightB} \quad (8)$$

$$\text{otherwise: new Right is RightA} \quad (9)$$

As for global distribution characteristics also, the CPU 225 can similarly judge sameness or non-sameness by setting left and right widths for each node.

Here, the CPU 225 examines whether control limits (ranges of wavelength and magnitude) for judging anomaly or normalcy of etching exist among the parameters set in the step S101. In the case where the control limits exist, the CPU 225 judges whether the magnitude of a peak existing in the wavelength range prescribed by the control limits deviates from the magnitude range prescribed in the control limits. In the case where the magnitude deviates, it is judged to be anomaly.

As such control limits, ones determined as follows may be used. That is to say, peak characteristics are obtained from OES data on past work of the same recipe (etching process conditions such as gas flow rate, electric conditions for plasma generation, pressure and temperature) and the same wafer structure, and control limits (wavelength range, upper limit, lower limit and target of peak magnitude in the wavelength range) are determined from 3σ on the basis of the average of emission magnitude and variation between wafers. Or, design of experiments may be employed to set several kinds of etching process conditions, and the average and variation of emission magnitude over experiments are obtained in order to set control limits.

In the case where control limits are not set in the step S101, the CPU 225 obtains probability of deviation (probability of occurrence of error value from the average obtained from an assumed distribution) for each wafer on the basis of the average and standard deviation of peak characteristics or global distribution characteristics (for example, using magnitude). Then, anomaly or normalcy of etching is judged depending on whether the probability of deviation exceeds a prescribed value.

Or, the CPU 225 may use cross validation in which a peak magnitude of one wafer is compared with the average and standard deviation summarized from other wafers' peaks, and judge anomaly or normalcy of etching by judging whether the magnitude exceeds a prescribed value such as the standard deviation multiplied by 3, for example.

After the judgment, the CPU 225 displays the result on the display unit 229 (Step S109).

Figure 12:
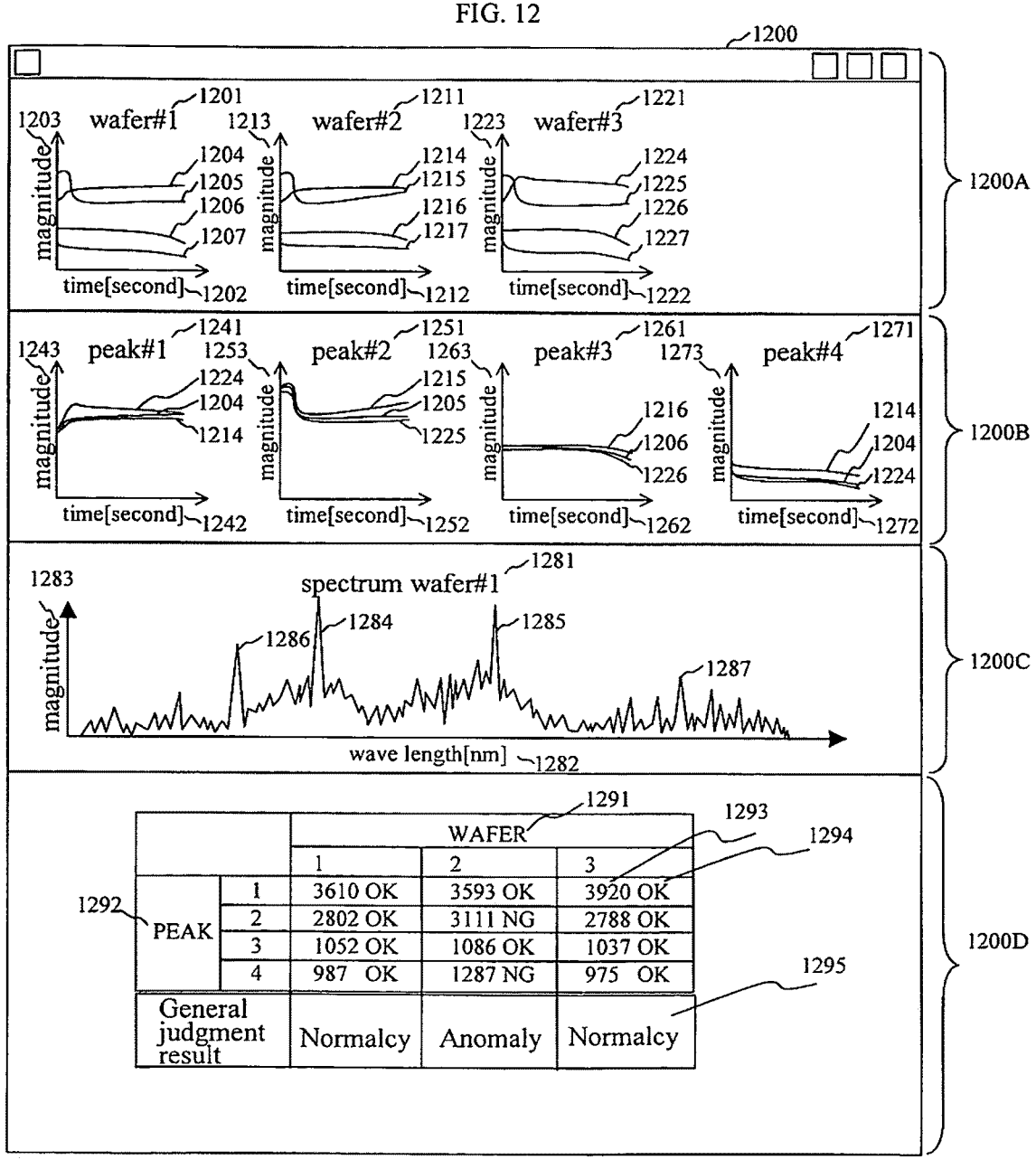
FIG. 12 is a view showing an example of a display screen.

FIG. 12 shows an example of display.

The CPU 225 displays the detected peaks on in-situ monitoring time scale for each wafer and for each peak (See the screen area 1200A and 1200B). Further, the CPU 225 displays the optical emission spectrum distribution used for the detection (See the area 1200C). Further, the CPU 225 displays the judgment result (See the screen area 1200D).

In detail, the screen area 1200A displays graphs with time 1202, 1212, 1222 as the horizontal axis and magnitude 1203, 1213, 1223 as the vertical axis. The graphs are displayed for respective wafers 1201, 1211, 1221. The graphs show in-situ time scale variation 1204-1207, 1214-1217, 1224-1227 of respective peaks (peak#1, peak#2, peak#3, peak#4).

The screen area 1200B displays graphs with time 1242, 1252, 1262, 1272 as the horizontal axis and magnitude 1243, 1253, 1263, 1273 as the vertical axis. The graphs are displayed for respective peaks 1241, 1251, 1261, 1271. The graphs show in-situ time scale variations (1204, 1214, 1224; 1205, 1215, 1225; 1206, 1216, 1226; 1207, 1217, 1227) of the respective peaks in the wafers (wafer#1, wafer#2, wafer#3, wafer#4).

The CPU 225 receives designation (by a wafer identifier) of the optical emission spectrum distribution to be displayed in the screen area 1200C through the input unit 228, and displays the designated optical emission spectrum distribution.

The screen area 1200D displays peak wavelengths 1293 and information 1294 indicating etching process' anomaly or normalcy obtained by the above-described method (for example, the judgment method based on deviation from the control limits) for common peaks of each wafer 1291. In the example of FIG. 12, "NG" indicates deviation from the control limits, and "OK" existence in the range of the control limits.

Further, the CPU 225 may obtain and display general judgment result 1295 of etching process on the basis of the number of peaks judged to be anomaly. For example, the CPU 225 may display the general judgment result 1295 as anomaly even if one "NG" exists. Depending on wafers as the processing objects, it is possible to determine suitably the number of "NG" in existence as the standard of the "anomaly" judgment.

Next, the CPU 225 formulates a relation between the detected peak characteristics and measurement results by using the multiple regression analysis (Step S111 in FIG. 9).

In detail, in association with a wafer, first the CPU 225 sets, as output data y, data (for example, line width or film thickness) of the measurement results obtained by the measurement apparatus 221, and sets the peak characteristics as input data x.

In some wafers, a peak is not detected. A peak that is not detected as a peak cannot be used as the input data. Further, a peak that does not change in its emission magnitude among wafers cannot be used as the input data also for regression analysis.

Then, the CPU 225 performs the multiple regression analysis. In detail, when the following equation (10) is employed as a model, its coefficients $a_i$ (i=0–n; n is the number of input data items) are estimated by the following equation (1).

$$y = a_0 + a_1 x_1 + \ldots + a_n x_n = a^T x \tag{10}$$

$$a = (X^T X)^{-1} X^T y \tag{11}$$

Here, X indicates an input data matrix where the number of row is the number of samples $n_{sample}$ and the number of column is n+1. The symbol y indicates $n_{sample}$ output vector.

Then, the CPU 225 obtains the optical spectrum distribution of OES data for the measurement result prediction object designated by the operator, detects peaks, and estimates the measurement results on the basis of the model formula (10).

Using such multiple regression analysis, the CPU 225 can obtain optical emission spectrum distribution of a wafer under processing during work of the etching process, and thereby predict measurement results while monitoring the optical emission before measurement after the process.

According to the peak characteristic detection method of the present invention, it is possible to detect 20-30 or more peaks at once. It is important for anomaly/normalcy judgment of etching whether it is possible to judge which peak has a large effect on measurement results.

Thus, the CPU 225 judges necessity of input x for output y in the multiple regression analysis. That is to say, the CPU 225 performs statistical test about whether a $a_i$ coefficient $a_i$ is zero "0" or not. It is assumed that distribution of a value that a coefficient can take in the multiple regression analysis is t-distribution. Using the following equation (12) as a model, the CPU 225 can calculate the t-statistics according to the following equations (13)-(19). Then, probability of the t-statistics obtained on the basis of the t-distribution is judged.

$$y = a_0 + a_1 x_1 + \ldots + a_n x_n \tag{12}$$
$$= a_0 + a^T x$$

$$X = \begin{bmatrix} x^T[1] \\ x^T[2] \\ \vdots \\ x^T[n_{sample}] \end{bmatrix} \tag{13}$$

$$= \begin{bmatrix} x[1][1] & x[1][2] & \ldots & x[1][n] \\ x[2][1] & x[2][2] & & x[2][n] \\ \vdots & & \ddots & \vdots \\ x[n_{sample}][1] & x[n_{sample}][2] & \ldots & x[n_{sample}][n] \end{bmatrix}$$

$$s[i\#][j\#] = \sum_{k\#=1}^{n_{sample}} \left( \frac{x[k\#][i\#] -}{\underset{l\#}{avex}[l\#][i\#]} \right) \left( \frac{x[k\#][j\#] -}{\underset{l\#}{avex}[l\#][j\#]} \right) \tag{14}$$

$$S = \begin{bmatrix} s[1][1] & s[1][2] & \ldots & s[2][n] \\ s[2][1] & s[2][2] & & s[2][n] \\ \vdots & & \ddots & \vdots \\ s[n][1] & s[n][2] & \ldots & s[n][n] \end{bmatrix} \tag{15}$$

$$S^{-1} = \begin{bmatrix} s^{inv}[1][1] & s^{inv}[1][2] & \ldots & s^{inv}[2][n] \\ s^{inv}[2][1] & s^{inv}[2][2] & & s^{inv}[2][n] \\ \vdots & & \ddots & \vdots \\ s^{inv}[n][1] & s^{inv}[n][2] & \ldots & s^{inv}[n][n] \end{bmatrix} \tag{16}$$

$$Se = \sum_{i\#} (y^*[i\#] - \hat{y}[i\#])^2 \tag{17}$$

-continued $$MSe = \frac{Se}{n_{sample} - n - 1} \tag{18}$$

$$t_0[i\#] = \frac{|a_{i\#}|}{\sqrt{s^{inv}[i\#][i\#] \times MSe}} \tag{19}$$

Here, symbols i#, j# and k# are indexes. The superscript "*" of output y in the equation (17) means an actually-achieved value (a value set in the screen). The hat "^" means an estimated value (a value obtained by the equation (12)).

The CPU 225 evaluates the standard error $\sigma^{2*}$ (the following equation (20)) in each model by deleting a large value of t-statistics for each input x and repeating the multiple regression analysis. As a result, assuming that the combination of peaks giving the minimum standard error can best express the phenomenon affecting the measurement result of the etching, it is possible to limit peaks that become effective for estimation of measurement results. In other words, it is possible to reduce the number of peak characteristics introduced into the model formula, reducing the number of terms, and to identify peak characteristics that can give sufficiently-satisfying prediction accuracy with a smaller number of peak characteristics as far as possible.

$$\sigma^{2*} = \sqrt{\frac{Se}{n_{sample} - n}} \tag{20}$$

After the end of calculation process, the CPU 225 displays the results (the model formula of the multiple regression analysis and predicted values of measurement results) on the screen (Step S112).

Here, the CPU 225 can judge anomaly or normalcy of the etching process depending on whether the predicted values of measurement results deviate from the previously-set threshold range, and can display the judgment result.

Hereinabove, the flow of processing for judging anomaly or normalcy of an etching process according to the first mode has been described.

[Second Mode]

Next, will be described a method judging anomaly or normalcy of an etching process by detecting time-series variation of etching among wafers by using a ratio of optical emission spectrum distributions (spectral ratio).

In particular, this method detects time-series variation of etching itself in the case where there exists not only time-series variation of etching itself but also time-series variation relating to another factor such as an optical emission monitoring system of an optical emission spectrometry. This method is referred to as "spectral ratio judgment method".

Figure 13:
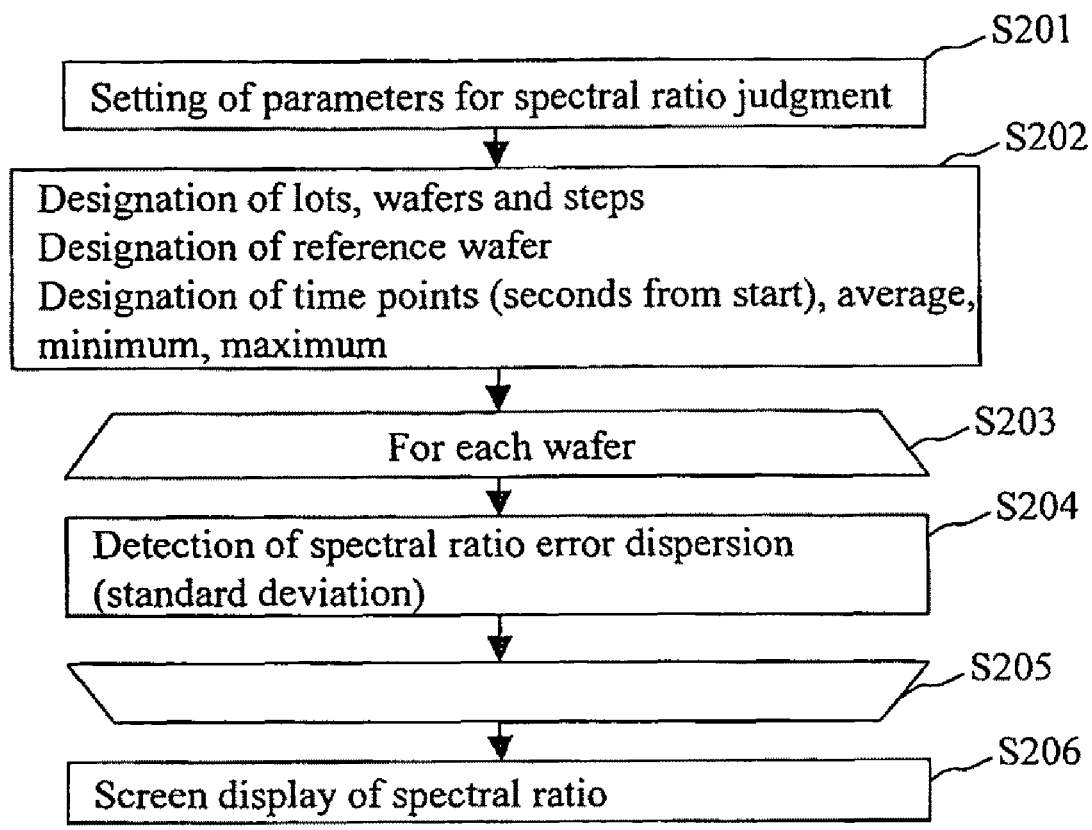
FIG. 13 is a flowchart showing an anomaly/normalcy judgment method using a spectral ratio.

FIG. 13 is a flowchart showing a judgment processing using a spectral ratio.

First, based on input values from an operator, the CPU 225 sets parameters for the spectral ratio judgment (Step S201). In the present method, a standard deviation is obtained by using smoothing and a limited wavelength range, and thus the CPU 225 sets the number of reference points in a moving-average operation for smoothing and the number of samples for standard deviation calculation. Or, a wavelength range (the minimum wavelength and the maximum wavelength) becoming the evaluation object may be set.

Further, the CPU 255 sets threshold values for judgment. These threshold values may be ones prepared in the past spectral ratio judgment that was performed by using time-series variation among wafers processed with the same recipe.

Next, similarly to the processing in the above step S102, the CPU 225 sets wafers that become objects of the spectral ratio judgment on the basis of input values from the operator (Step S202).

Then, the CPU 225 reads an optical spectrum distribution of OES data satisfying the conditions set in S202 from the database 223, and performs the processing in the step S103 and the following.

First, the CPU 225 detects spectral ratio error dispersion (standard deviation) for each wafer (Steps S203-S205).

FIG. 14 shows a method in which the spectral ratio error dispersion is obtained and anomaly or normalcy of the etching process is judged.

First, the CPU 225 determines an optical emission spectrum distribution as baseline, and obtains respective ratios of the other optical emission spectrum distributions 1401 to the baseline, to obtain spectral ratios 1411 (the following equation (21)). In FIG. 14, the optical emission spectrum distribution having the maximum magnitude is selected as the baseline to obtain ratios.

Then, the CPU 225 smoothes the spectral ratios by moving average (the following equation (22)).

$$\text{ratio}[i\#] = \frac{mag^{sample}[i\#]}{mag^{base}[i\#]} \quad (21)$$

$$\text{ratio}^{MA}[i\#] = MA(i\#, {}^{range}N^{MA}_{HALF}, \text{ratio}) \quad (22)$$

Here, the symbol i# indicates an index for wavelength. The symbol ${}^{range}N^{MA}_{HALF}$ indicates the number 1422 of reference points in moving-average operation on one side. The superscript "MA" in the upper right of "ratio" means moving average. The term MA(i#, N, data) indicates a procedure of obtaining moving average of a variable "data" on both side where the number of the one side is N, with respect to the center at the position i#.

Then, the CPU 225 obtains the spectral ratio error standard deviation. First an error between a spectral ratio and its moving average is obtained, and obtains the standard deviation 1431 at each wavelength position in the range where the one side is ${}^{range}N^{sigma}_{HALF}$.

$$e_{ratio}[i\#] = \text{ratio}[i\#] - \text{ratio}^{MA}[i\#] \quad (23)$$

$$\sigma_{ratio}[i\#] = \underset{j\#=i\#-{}^{range}N^{sigma}_{HALF}...i\#+{}^{range}N^{sigma}_{HALF}}{stdev} \cdot e_{ratio}[j\#] \quad (24)$$

Here, stdev data[i#] indicates an operation of obtaining the standard deviation over the index i#.

Here, one point should be noted. In this calculation, the spectral ratio error standard deviation becomes a large value not only owing to large dispersion but also owing to large inclination of spectral ratio as shown at 1433.

Thus, by correcting the inclination, it becomes possible to detect only wavelength positions where the dispersion is large. In detail, the CPU 225 obtains and smoothes inclination Δ by the following equations (25) and (26), and obtains the corrected spectral ratio error standard deviation $\sigma^{correct}_{ratio}$ 1441 by the equation (27).

$$\Delta^{MA}_{ratio}[i\#] = \text{ratio}^{MA}[i\#] - \text{ratio}^{MA}[i\#-1] \quad (25)$$

$$\Delta^{MA,MA}_{ratio}[i\#] = MA(i\#, {}^{range}N^{MA}_{HALF}, \Delta^{MA}_{ratio}) \quad (26)$$

$$\sigma^{correct}_{ratio}[i\#] = \frac{\sigma_{ratio}[i\#]}{|\Delta^{MA,MA}_{ratio}[i\#]|} \quad (27)$$

Then, if the obtained spectral ratio error standard deviation $\sigma^{correct}_{ratio}$ 1441 exceeds the previously-set threshold value (lower limit) $\sigma^{LCL}_{ratio}$ 1442, the CPU 225 judges that there is difference at that wavelength position in etching process among etching processes or there is anomaly (the following equation (28)).

$$\sigma^{correct}_{ratio}[i\#] \geq \sigma^{LCL}_{ratio}: \text{Magnitude is changed.} \quad (28)$$

Lastly, the CPU 225 displays a spectral ratio display screen. This screen shows the judgment result and the various graphs shown in FIG. 14.

Here, the CPU 255 may detect peaks of the optical spectrum distribution before the processing of S203 and perform processing of eliminating peaks (over-scale peaks) only at positions of reaching the maximum magnitude of optical emission monitoring. In the processing on and following S203, such processing of obtaining spectral ratios may be continued using the optical emission spectrum distribution from which the over-scale peaks have been eliminated.

[Third Mode]

Next, will be described a method of judging anomaly or normalcy of an etching process by evaluating the early process of etching.

Figure 15:
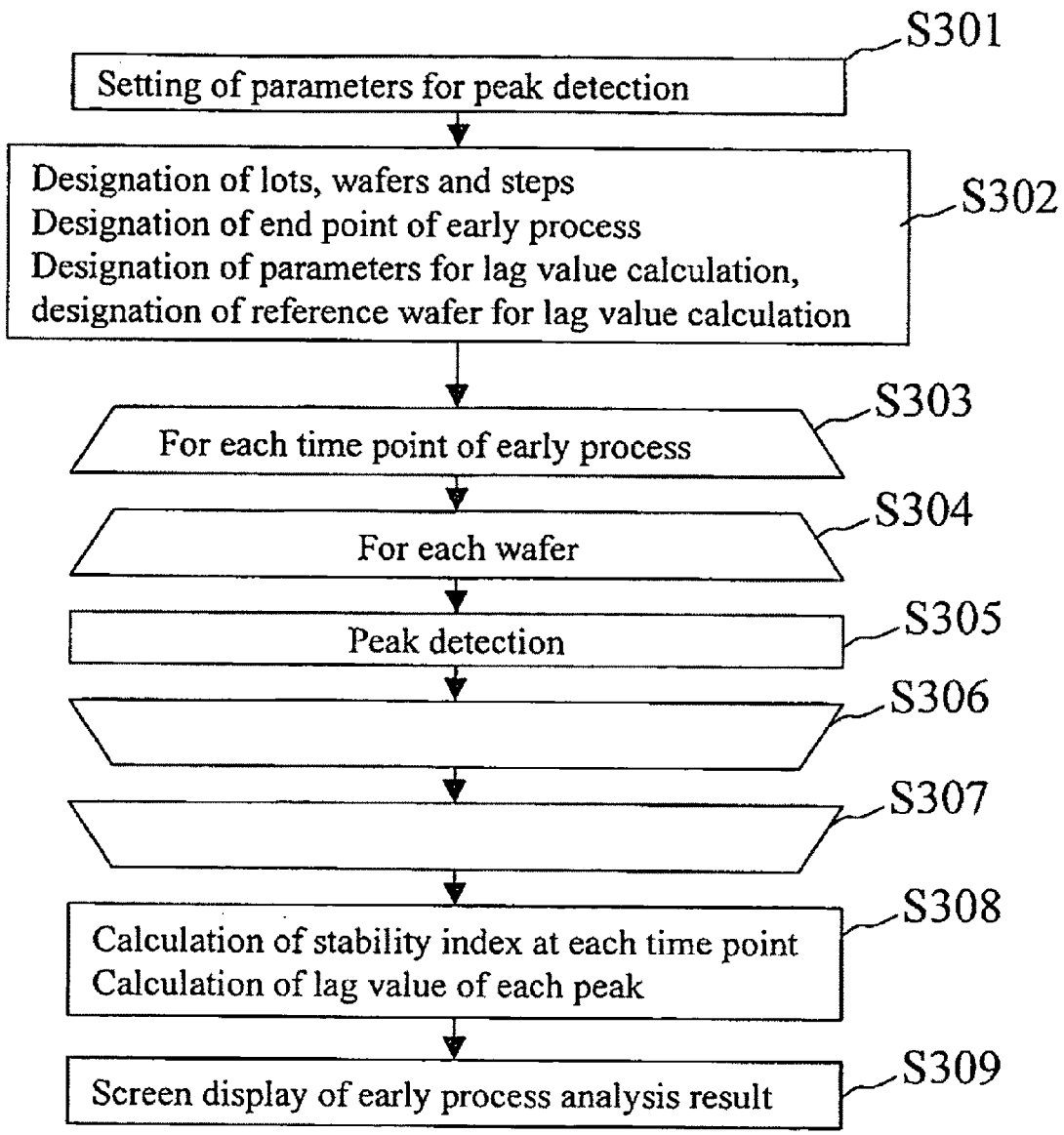
FIG. 15 is a flowchart showing an anomaly/normalcy judgment method in an early process.

FIG. 15 shows a flow of such a judgment method. Here, the early process is analyzed by calculating a stability index used for analyzing the time required for stabilization of an unstable state at the start time of etching and by calculating a lag value used for analyzing the starting-up (reaction lag) in etching process of a wafer in comparison with etching process of a certain wafer.

Similarly to the above step S101, the CPU 225 sets parameters for peak detection on the basis of input values from an operator (Step S301).

Further, the CPU 225 sets lots, wafers and steps for specifying object optical emission spectrum distributions of OES data (Step S302).

In detail, based on the input values from the operator, the CPU 225 sets a time point at which the early process from the start of the etching process seems to end, in order to determine a time range of the early process on in-situ time scale, or a sets a time point for determining the time range that becomes the analysis object as the early process. Further, the CPU 225 sets parameters used for lag value calculation and a baseline wafer used for calculation of the lag value. The parameters used for lag value calculation are start and end times, a lag evaluation range (delay side and advance side), a time interval for data in a comparison range. Meaning of these parameters will be shown in describing lag value calculation processing (Step S308) for each peak.

After obtaining OES data as the object, the CPU 225 detects peaks in optical emission spectrum distribution of each wafer for each time point in the early process (Steps S303-S307).

Figure 16:
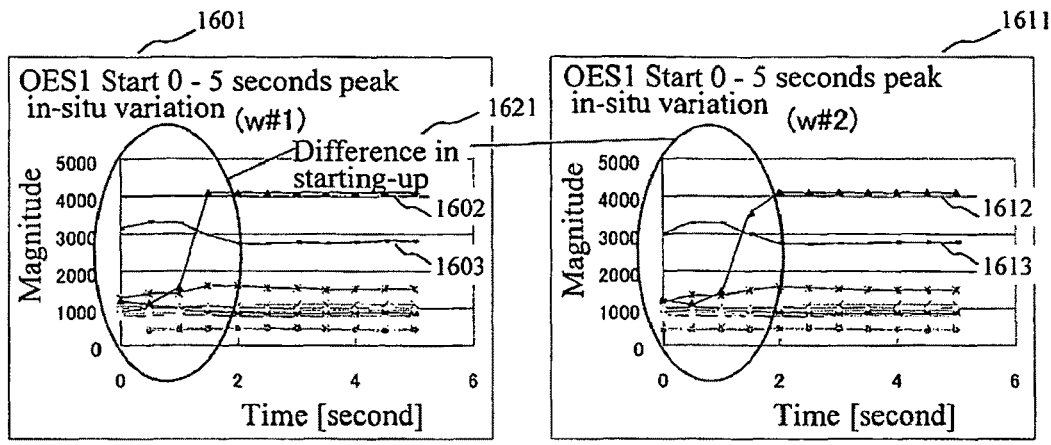
FIG. 16 is a graph of magnitude variation on an in-situ monitoring time scale.

FIG. 16 shows graphs in which detected peaks are arranged on in-situ time scale.

As for processes of two wafers, it is possible to confirm that there is a difference 1621 in the starting-up period as shown by the peaks 1602 and 1612, and that there is difference in dimensions of magnitude and its variation as shown by the peaks 1602 and 1603.

Then, the CPU 225 calculates a stability index at each time point, and calculates a lag value of each peak (Step S308).

First, a method of calculating a stability index will be described.

Figure 17:
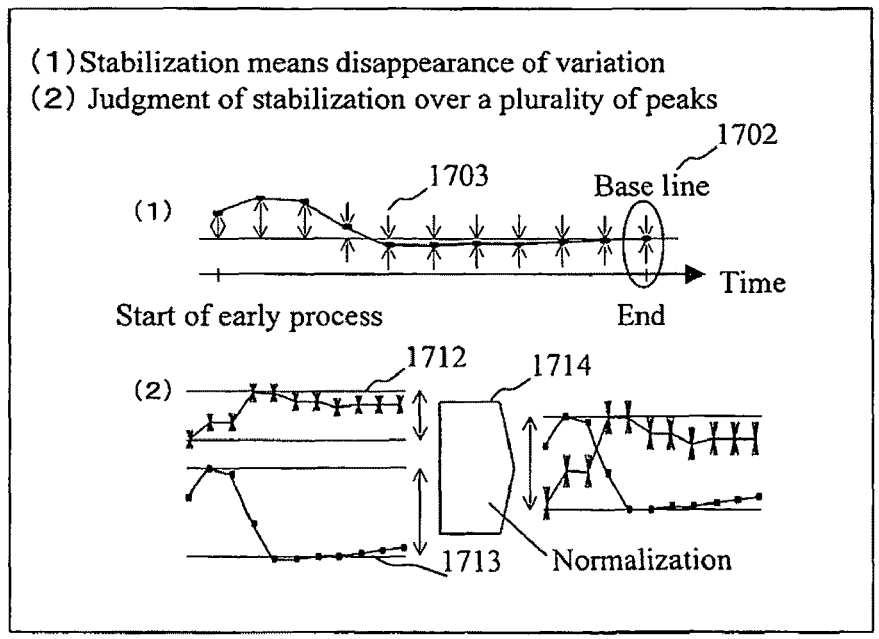
FIG. 17 is a diagram for explaining a stability index.

FIG. 17 shows the concept of a stability index. As shown in FIG. 16, although there is a difference in starting-up between wafers, magnitude converges into a certain value for any peak. Thus, using, as the base line 1702, the magnitude of the end time of the early process in which peak magnitude converges (in other words, a time point when a change of peak magnitude becomes within a prescribed range), the CPU 225 obtains a difference (scale) of magnitude 1703 at each time point. Further, since peaks are different from one another in scale of magnitude and its variation, the CPU 225 normalizes (1714) scale of magnitude variation about a plurality of peaks 1712 and 1713 in order to realize stabilization reflecting all the peaks.

As a normalization method, there is a method in which the maximum and minimum values are made to be equal for a plurality of peaks. However, by evaluating the scale of variation in relation to dispersion, it is possible to treat variation as statistically-normalized data when the dispersion follows the normal distribution, for example. For the calculation of the dispersion, magnitude difference (scale) at each time point in relation to the magnitude at the end time may be used.

An index expressing such stabilization is referred to as a stability index and can be defined by the following equation.

$$Stability_{initial}[i\#] = \sum_{j\#}^{N_{peak}} \left( \frac{mag[j\#][i\#] - mag[j\#][\#end]}{stdevmag[j\#][k\#]} \right)^2 \quad (29)$$

Here, the symbols i# and k# are indexes each indicating a time point. The symbol j# is an index indicating a peak. The symbol $N_{peak}$ indicates the total number of detected peaks. And, the symbol #end is an index number meaning the end time.

$$\underset{k\#}{stdevd}[k\#] \quad (30)$$

indicates operation of obtaining the standard deviation of data d over index k#.

According to the above equation, statistical test of the stabilization can be performed by using chi-square while setting the significance level, since the stability index $Stability_{initial}$ follows the chi-square distribution with the number of peak $N_{peak}$ degree of freedom when the peak magnitude mag follows the normal distribution.

Figure 18:
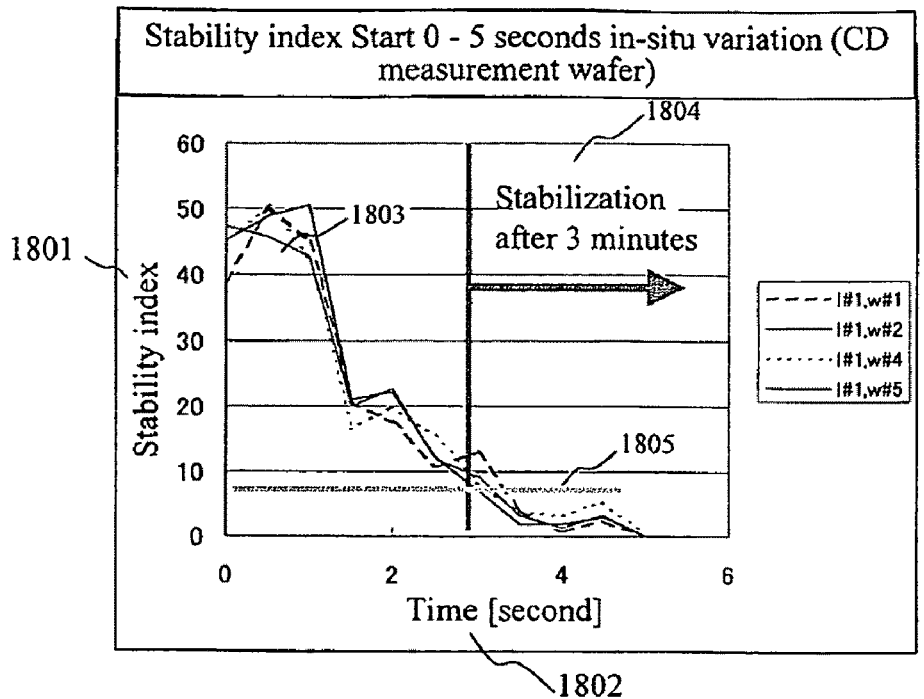
FIG. 18 is a diagram showing an example of a result of calculation of a stability index.

FIG. 18 shows a calculation result of stability index 1801 concerning four wafers. The CPU 225 calculates the stability index 1801 at regular intervals of time 1802.

In the example of FIG. 18, in-situ time scale variation 1803 of stability index becomes smaller gradually, and is nearly stabilized at a time point 1804 of about 3 seconds.

The CPU 225 can judge a time point (at 4 seconds in the example of FIG. 18) of stabilization by comparing the stability index with the chi-square value 1805 with a set significance level (for example, 95%) and a set degree of freedom (the number of wafers, fifteen).

Then, the CPU 225 can judge anomaly or normalcy of the etching process depending on whether the point of stabilization is later than a previously-determined time.

In the case where there is a peak characteristic that can not be detected with respect to a wafer, the CPU 225 may interpolate the peak characteristic at the point of non-detection (data filling) by using the average of peak characteristic values before and after the point in question in time-series. Or, the CPU 225 may ignore the peak characteristics at the wavelength in question (where the non-existence of a peak characteristic has been detected) with respect to all the wafers.

Next, a lag value calculation method will be described.

Figure 19:
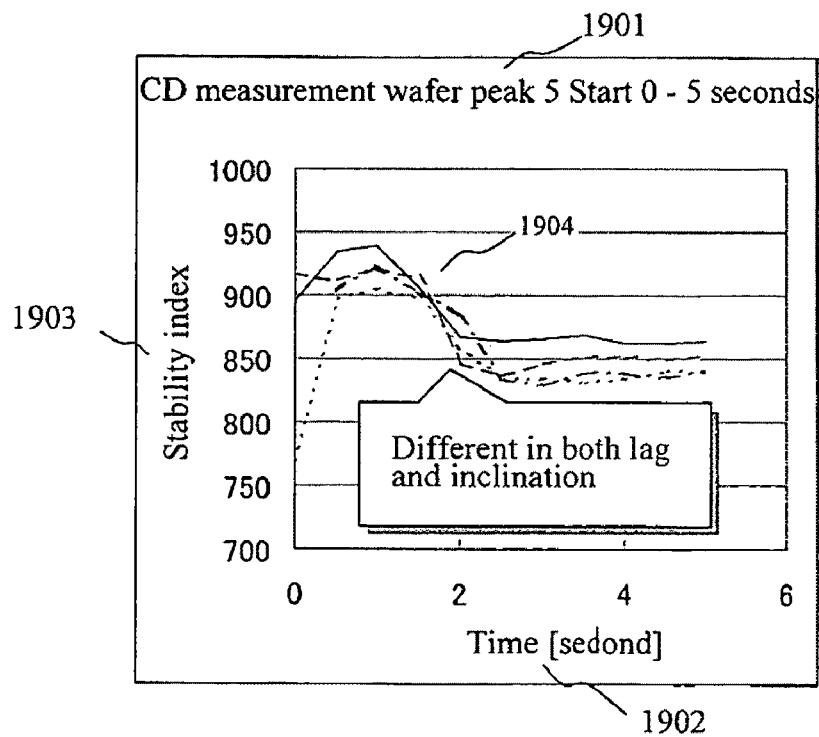
FIG. 19 is an in-situ monitoring time scale graph of peak magnitude variation between wafers.

FIG. 19 shows peak magnitude variations 1901 of each wafer at some peak on in-situ time scale. Here, the horizontal axis is time, and the vertical axis magnitude. In the example of FIG. 19, it can be confirmed that peak magnitude variations 1904 delays along the time 1902. However, there are differences in direction of magnitude 1903 among wafers. In other words, not only delay but also inclination of variation is different.

Figure 20:
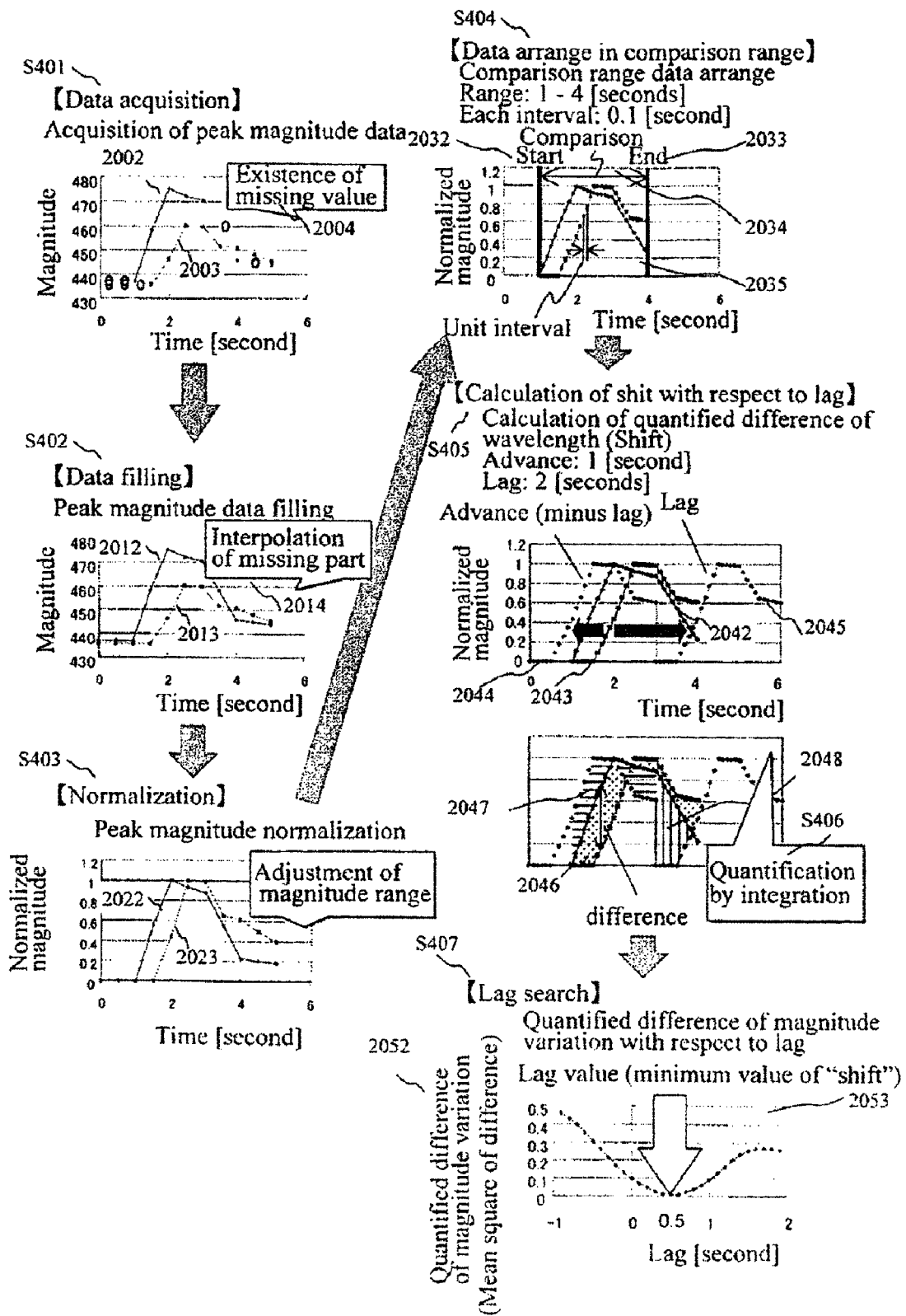
FIG. 20 is an explanatory diagram showing a method of obtaining a lag value.

FIG. 20 is a diagram for explaining a method of obtaining a lag value.

First, the CPU 225 obtains data of peak magnitude variation as the object (Step S401). FIG. 20 shows peak magnitude variation 2002 that becomes the criterion and peak magnitude variation 2003 whose lag is to be obtained.

Sometimes, peak magnitude variation has a missing value 2004 since a peak can not be detected at some time point.

Thus, the CPU 225 interpolates respective values 2014 into missing values by data filling (Step S402), to obtain magnitude variations 2012 and 2013. Here, in the case where there is a peak characteristic that can not be detected with respect to a wafer, the CPU 225 may ignore the peak characteristics at the wavelength in question (where the non-existence of the peak characteristic has been detected) with respect to all the wafers.

Then, the CPU 225 normalizes the data to make the magnitude ranges coincide with each other such that the minimum becomes 0 and the maximum becomes 1, as shown by the magnitude variations 2022 and 2023 (Step S403).

The CPU 225 arranges data in the comparison range (Step S404). In detail, the CPU 225 limits the comparison range 2034 by previously-determined start time 2032 and end time 2033. And, to obtain a fine lag value, the CPU 225 interpolates magnitude on a short time scale 2035.

Then, the CPU 225 calculates a shifting value that quantifies a difference between two peak magnitude variations (Step S405). In detail, the CPU 225 shifts the magnitude variation 2043 (whose lag value is to be obtained) in the advance direction and delay direction to obtain magnitude variations 2044 and 2045.

Then, the CPU 225 obtains a difference from the variation 2042 as the base variation, and quantifies the difference by integration (Step S406). In the example of FIG. 20, the shifting value becomes the part of the areas 2046, 2047 and 2048.

Then, the CPU 225 obtains a position at which the shifting value becomes the minimum, and determines this shifting value as the lag value (lag search [Step S407]). The shifting value is a difference with lag (difference square mean value) 2052 of variation obtained by averaging integral of difference over the overlapped time range. The position at which the shifting value becomes the minimum becomes the lag value 2053.

Thus, the lag value can be calculated as described above.

The CPU 225 can judge anomaly or normalcy of etching process by judging whether the lag value exceeds a previously-determined value.

Lastly, the CPU 225 displays an early process analysis result screen that shows the stability index calculation result, the peak lag value calculation result, and the judgment result on anomaly or normalcy of etching process for each wafer and for each peak in a table on the display unit 229 (Step 309 of FIG. 15). Here, the graphs of the calculation process shown in FIG. 20 may be displayed successively or at once.

Hereinabove, the etching process state judgment system according to one embodiment of the present invention has been described.

According to the above embodiment, it is possible to detect peaks automatically from optical emission spectrum distribution at the time of etching process without assuming a substance, to detect state difference among wafers, and to judge existence of anomaly.

Further, it is possible to detect not only peaks but also global optical emission spectrum distribution to be used for judgment.

Further, in etching of a plurality of wafers, a state of optical emission changes each time. This is because the configuration (quantity ratios and contaminants) of substances in etching reaction relating to plasma in a chamber changes each time of work. However, there is also time-series variation that occurs each time of work in relation to an optical emission monitoring system itself by an optical emission spectrometry, such as adhesion of substances to a window for observing the inside of the chamber, for example. According to the present invention, it is possible to correct this variation having no relation to etching reaction, so that wafers can be compared regarding their optical emission spectrum distributions.

Further, according to the present embodiment, in order to realize a prescribed shape on a wafer, it is possible to determine a relation of automatically-detected peaks on optical emission spectrum distribution with a shape or an etching rate, and to predict a shape on the wafer or an etching rate on the basis of data of optical emission spectrum distribution.

Further, according to the present embodiment, in order to detect anomaly in the course of etching process, it is possible in particular to detect difference between wafers in the early etching process relating to stabilization of etching reaction. Further, it is possible to quantify a time until peaks of optical emission are stabilized and starting-up lag in realization of a steady state, so that differences of wafers can be automatically compared.

Thus, if OES data in the past starting-up of etching equipment have been evaluated previously, it is possible to judge whether prescribed reaction is occurring at the time of starting up of the same type of equipment by obtaining OES data. This can make starting up of the equipment more efficient.

In the case of high-volume manufacturing, OES data can be obtained each time of work of wafers, and thus anomaly can be detected each time of work. Further, since peaks can be detected automatically, it is possible to monitor variation of magnitude of each peak automatically. Particularly, since measurement results can be predicted from peaks, thus it is possible to obtain measurement results without actual measurement, to detect anomaly in product quality, and to correct the etching recipe on the basis of time-series variation of peaks.

Further, at the time of maintenance, OES data can be utilized to verify the performance of equipment. Accordingly, it is possible to reduce test items for verification of equipment performance, and to verify functions and performance that can not be verified conventionally.

The processing of the etching anomaly/normalcy judgment method of the present invention can be applied to a production method that uses at least a means for obtaining optical emission spectrum distribution and performs an anomaly/normalcy judgment method, even if the process in the production method is not etching and the object of the process is neither a wafer nor a semiconductor device.

The invention claimed is:

1. An etching process state judgment method comprising:
a spectral data obtaining step, in which an optical emission spectrum distribution is obtained by monitoring optical emission during an etching process of a plurality of wafers;
a peak detection step, in which peaks are detected from the optical emission spectrum distribution at a specific time point during the etching process by detecting a charge in emission magnitude along with a wavelength, to obtain peak characteristics;
a common peak identifying step, in which peaks common to the wafers are identified among the peaks detected in the peak detection step; and
a state detection step, in which the peak characteristics are compared regarding the common peaks, to detect a state of each wafer in the etching process, wherein:
in the peak detection step, peak candidates specified by rapid rising-up and rapid falling-down of magnitude are extracted from the optical emission spectrum distribution;
optical spectrum distribution magnitude $M_{Left\_Bottom}$ corresponding to a wavelength (referred to as "left-side rising-edge wavelength") $W_{Left\_Bottom}$ on a shorter wavelength side of a peak;
optical emission spectrum distribution magnitude $M_{Top}$ corresponding to a wavelength $W_{Top}$ at which optical emission spectrum distribution magnitude becomes a maximum;
optical emission spectrum distribution magnitude $M_{Right\_Bottom}$ corresponding to a wavelength (referred to "right-side rising-edge wavelength") $W_{Right\_Bottom}$ on a longer wavelength side of the peak;
a difference (referred to as "left-side peak height") $M_{Left\_H}$ between the maximum $M_{Top}$ of the optical emission spectrum distribution magnitude and the optical emission spectrum distribution magnitude $M_{Left\_Bottom}$ of the left-side rising-edge wavelength;
a difference (referred to as "right-side peak height") $M_{Right\_H}$ between the maximum $M_{Top}$ of the optical emission spectrum distribution magnitude and the optical emission spectrum distribution magnitude $M_{Right\_Bottom}$ of the right-side rising-edge wavelength;
an average $M_{AVE\_H}$ between the left-side peak height $M_{Left\_H}$ and the right-side peak height $M_{Right\_H}$;
an aspect ratio (referred to as "left-side aspect ratio") Left_AR obtained by dividing the left-side peak height $M_{Left\_H}$ by a difference $W_{Left\_W}$ between the wavelength $W_{Top}$ at which the optical emission spectrum distribution magnitude becomes the maximum and the left-side rising-edge wavelength $W_{Left\_Bottom}$;
an aspect ratio (referred to as "right-side aspect ratio") Right_AR obtained by dividing the right-side peak height $M_{Right\_H}$ by a difference $W_{Right\_W}$ between the wavelength $M_{Top}$ at which the optical emission spectrum distribution magnitude becomes the maximum and the right-side rising-edge wavelength $W_{Right\_Bottom}$; and
an average AVE_AR between the left-side aspect ratio Left_AR and the right-side aspect ratio Right_AR;
are obtained; and
peak candidates for which the average AVE_AR and the average $M_{AVE\_H}$ are more than or equal to respective prescribed values are selected as peaks.

2. An etching process state judgment method of claim 1, wherein:
the peak characteristics includes at least one of:
optical spectrum distribution magnitude $M_{Left\_Bottom}$ corresponding to a wavelength (referred to as "left-side rising-edge wavelength") $W_{Left\_Bottom}$ on a shorter wavelength side of a peak;
optical emission spectrum distribution magnitude $M_{Top}$ corresponding to a wavelength $W_{Top}$ at which optical emission spectrum distribution magnitude becomes a maximum;
optical emission spectrum distribution magnitude $M_{Right\_Bottom}$ corresponding to a wavelength (referred to "right-side rising-edge wavelength") $W_{Right\_Bottom}$ on a longer wavelength side of the peak;
a difference (referred to as "left-side peak height") $M_{Left\_H}$ between the maximum $M_{Top}$ of the optical emission spectrum distribution magnitude and the optical emission spectrum distribution magnitude $M_{Left\_Bottom}$ of the left-side rising-edge wavelength;
a difference (referred to as "right-side peak height") $M_{Right\_H}$ between the maximum $M_{Top}$ of the optical emission spectrum distribution magnitude and the optical emission spectrum distribution magnitude $M_{Right\_Bottom}$ of the right-side rising-edge wavelength;
an average $M_{AVE\_H}$ between the left-side peak height $M_{Left\_H}$ and the right-side peak height $M_{Right\_H}$;
an aspect ratio (referred to as "left-side aspect ratio") Left_AR obtained by dividing the left-side peak height $M_{Left\_H}$ by a difference $W_{Left\_W}$ between the wavelength $W_{Top}$ at which the optical emission spectrum distribution magnitude becomes the maximum and the left-side rising-edge wavelength $W_{Left\_Bottom}$;
an aspect ratio (referred to as "right-side aspect ratio") Right_AR obtained by dividing the right-side peak height $M_{Right\_H}$ by a difference $W_{Right\_W}$ between the wavelength $W_{Top}$ at which the optical emission spectrum distribution magnitude becomes the maximum and the right-side rising-edge wavelength $W_{Right\_Bottom}$; and
an average AVE_AR between the left-side aspect ratio Left_AR and the right-side aspect ratio Right_AR.

3. An etching process state judgment method of claim 1, comprising:
a peak elimination step, in which the peaks detected in the peak detection step are eliminated from the optical emission spectrum distribution, to obtain a peak-eliminated optical emission spectrum distribution;
a global distribution characteristics calculation step, in which a plurality of magnitudes at respective prescribed wavelength positions are obtained from the peak-eliminated optical emission spectrum distribution, to obtain global distribution characteristics indicating global variation of the optical emission spectrum distribution; and
a state detection step, in which respective states of the wafers in the etching process are detected by comparing the global distribution characteristics.

4. An etching process state judgment method comprising:
a spectral data obtaining step, in which an optical emission spectrum distribution is obtained by monitoring optical emission during an etching process of a plurality of wafers;
a peak detection step, in which peaks are detected from the optical emission spectrum distribution at a specific time point during the etching process by detecting a change in emission magnitude along with a wavelength, to obtain peak characteristics;
a common peak identifying step, in which peaks common to the wafers are identified among the peaks detected in the peak detection step, and
a state detection step, in which the peak characteristics are compared regarding the common peaks, to detect a state of each wafer in the etching process, wherein:
the etching process state judgment method comprises:
a peak elimination step, in which the peaks detected in the peak detection step are eliminated from the optical emission spectrum distribution, to obtain a peak-eliminated optical emission spectrum distribution;
a global distribution characteristics calculation step, in which a plurality of magnitudes at respective prescribed wavelength positions are obtained from the peak-eliminated optical emission spectrum distribution, to obtain global distribution characteristics indicating global variation of the optical emission spectrum distribution; and
a correction step, in which with respect to a global distribution characteristic of a wafer that becomes a baseline, a ratio of a global distribution characteristic of another wafer is obtained at each wavelength position, and the original optical emission spectrum distribution of the another wafer is multiplied by the ratio at each wavelength position to obtain a corrected optical emission spectrum distribution from which difference between wafers has been eliminated; and
in the state detection step, peak characteristics of peaks in the corrected optical emission spectrum distribution obtained in the correction step are compared between wafers, to detect difference between states of the wafers in the etching process.

5. An etching process state judgment method comprising:
a spectral data obtaining step, in which an optical emission spectrum distribution is obtained by monitoring optical emission during an etching process of a plurality of wafers;
a peak detection step, in which peaks are detected from the optical emission spectrum distribution at a specific time point during the etching process by detecting a change in emission magnitude along with a wavelength, to obtain peak characteristics;
a common peak identifying step, in which peaks common to the wafers are identified among the peaks detected in the peak detection step; and
a state detection step, in which the peak characteristics are compared regarding the common peaks, to detect a state of each wafer in the etching process, the method further comprising:
a step, in which optical emission spectrum distributions are obtained for a plurality of wafers, and data indicating a surface shape or an etching rate of each of a wafer for which the optical emission spectrum distribution has been monitored are obtained;
a model formula calculation step, in which a model formula showing a relation between the surface shape or etching rate of the wafer and the peak characteristics of the optical emission spectrum distribution of the wafer is obtained by multiple regression analysis;
a step, in which an optical emission spectrum distribution is obtained by monitoring optical emission of a wafer as an object of prediction;
a step, in which peak characteristics is obtained from the optical emission spectrum distribution of the wafer as the object of prediction; and
a step, in which the peak characteristics of the optical emission spectrum distribution of the wafer as the object of prediction are used to estimate a surface shape or an etching rate of the wafer as the object of prediction by using the model formula.

6. An etching process state judgment method comprising:
a spectral data obtaining step, in which an optical emission spectrum distribution is obtained by monitoring optical emission during an etching process of a plurality of wafers;
a peak detection step, in which peaks are detected from the optical emission spectrum distribution at a specific time point during the etching process by detecting a change in emission magnitude along with a wavelength, to obtain peak characteristics;
a common peak identifying step, in which peaks common to the wafers are identified among the peaks detected in the peak detection step; and
a state detection step, in which the peak characteristics are compared regarding the common peaks, to detect a state of each wafer in the etching process, the method further comprising:
a step, in which optical emission spectrum distributions are obtained for a plurality of wafers, and data indicating a surface shape or an etching rate of each of a wafer for which the optical emission spectrum distribution has been monitored are obtained;
a model formula calculation step, in which a model formula showing a relation between the surface shape or etching rate of the wafer and the peak characteristics of the optical emission spectrum distribution of the wafer is obtained by multiple regression analysis;
a step, in which an optical emission spectrum distribution is obtained by monitoring optical emission of a wafer as an object of prediction;
a step, in which peak characteristics is obtained from the optical emission spectrum distribution of the wafer as the object of prediction; and
a step, in which the peak characteristics of the optical emission spectrum distribution of the wafer as the object of prediction are used to estimate a surface shape or an etching rate of the wafer as the object of prediction by using the model formula, wherein:
in the model formula calculation step, a number of peak characteristics that are introduced into the model formula among the peak characteristics detected in the peak detection step is reduced.

7. An etching process state judgment method comprising:
a spectral data obtaining step, in which an optical emission spectrum distribution is obtained by monitoring optical emission during an etching process of a plurality of wafers;
a peak detection step in which peaks are detected from the optical emission spectrum distribution at a specific time point during the etching process by detecting a change in emission magnitude along with a wavelength, to obtain peak characteristics;
a common peak identifying step, in which peaks common to the wafers are identified among the peaks detected in the peak detection step; and
a state detection step, in which the peak characteristics are compared regarding the common peaks, to detect a state of each wafer in the etching process, further comprising:
a step of obtaining an optical emission spectrum distribution at regular intervals between a start of the etching process and an end point of a prescribed early process;
a step of arranging on time scale the peak characteristics detected in the peak detection step;
a step of normalizing the peak characteristics by using a maximum value and a minimum value on a time scale for each peak characteristic;
a step of obtaining a stability index, in which a difference between a peak characteristic at each point and the peak characteristic at the end point of the early process is divided by a standard deviation of the peak characteristic on a time scale, and then a quotient is squared, and the stability index is obtained as an average of the resultant peak characteristics at each point; and
a stabilization judgment step, in which the early process of etching is judged to be stabilized when an average of the stability index among the wafers becomes less than a prescribed value or a chi-square value at which a degree of freedom becomes a peak number.

8. An etching process state judgment method comprising:
a spectral data obtaining step, in which an optical emission spectrum distribution is obtained by monitoring optical emission during an etching process of a plurality of wafers;
a peak detection step, in which peaks are detected from the optical emission spectrum distribution at a specific time point during the etching process by detecting a change in emission magnitude along with a wavelength, to obtain peak characteristics;
a common peak identifying step, in which peaks common to the wafers are identified among the peaks detected in the peak detection step; and
a state detection step, in which the peak characteristics are compared regarding the common peaks, to detect a state of each wafer in the etching process, further comprising:
a step of obtaining an optical emission spectrum distribution at regular intervals between a start of the etching process and an end point of a prescribed early process;
a step of arranging on time scale the peak characteristics detected in the peak detection step;
a step of normalizing the peak characteristics by using a maximum value and a minimum value on a time scale for each peak characteristic;
a step of detecting a state of the etching process, in which:
a square of a difference between a normalized characteristic of a wafer that becomes a criterion and a normalized characteristic of another wafer at a same wavelength position is obtained while shifting a time of the normalized characteristic of the another wafer,
the square of the difference of the peak characteristic is time-averaged in a range in which the criterion normalized peak characteristic and a time-shifted normalized peak characteristic of the another wafer overlap in time;
a time shift value for which a time-average of the square of the difference becomes smallest is taken as a lag or advance, and a lag value is obtained as that time shift value; and
a state of the etching process is detected on a basis of a magnitude of the lag value.

9. An etching process state judgment method, comprising:
a spectral data obtaining step, in which an optical emission spectrum distribution is obtained by monitoring optical emission during an etching process of a plurality of wafers;
a peak detection step, in which peaks are detected from the optical emission spectrum distribution at a specific time point during the etching process, to obtain peak characteristics; and
a state detection step in which:
an optical emission spectrum distribution of a previously-determined criterion wafer is taken as baseline, and a spectral ratio of an optical emission spectrum distribution of another wafer with respect to the baseline is obtained at each wavelength position;

a standard deviation of the spectral ratio is obtained at each of wavelength positions arranged at intervals of a prescribed width;

a derivative of the spectral ratio is obtained at each of the wavelength positions arranged at intervals of the prescribed width;

a dispersion index is obtained by dividing the standard deviation by an absolute value of the derivative at each of the wavelength positions arranged at intervals of the prescribed width; and a change of a state of the another wafer with respect to the criterion wafer is detected on a basis of the dispersion index.

* * * * *